US006521808B1

(12) United States Patent
Ozkan et al.

(10) Patent No.: US 6,521,808 B1
(45) Date of Patent: Feb. 18, 2003

(54) PREPARATION AND USE OF A CATALYST FOR THE OXIDATIVE DEHYDROGENATION OF LOWER ALKANES

(75) Inventors: Umit S. Ozkan, Worthington, OH (US); Rick B. Watson, Columbus, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 09/506,677

(22) Filed: Feb. 17, 2000

(51) Int. Cl.[7] .......................... C07C 5/333; B01J 23/00; B01J 37/00

(52) U.S. Cl. ..................... 585/661; 585/662; 585/663; 502/234; 502/236; 502/239; 502/242; 502/243; 502/247; 502/248; 502/250; 502/439; 502/514

(58) Field of Search ............................. 585/661, 662, 585/663; 502/234, 236, 239, 242, 243, 247, 248, 250, 439, 514

(56) References Cited

U.S. PATENT DOCUMENTS

| | | | |
|---|---|---|---|
| 2,895,920 A | * 7/1959 | Janoski ................ 502/234 |
| 3,401,125 A | * 9/1968 | Jaffe .................. 502/219 |
| 3,637,527 A | * 1/1972 | Jaffe .................. 502/74 |
| 3,665,049 A | 5/1972 | Cornelius et al. |
| 4,176,089 A | * 11/1979 | Cull ................... 502/236 |
| 4,410,501 A | 10/1983 | Taramasso et al. |
| 4,458,096 A | 7/1984 | Phillips et al. |
| 4,480,135 A | 10/1984 | Esposito et al. |
| 4,547,557 A | * 10/1985 | McDaniel ............. 526/106 |
| 4,666,692 A | 5/1987 | Taramasso et al. |
| 4,695,662 A | 9/1987 | Vora |
| 4,701,428 A | 10/1987 | Bellussi et al. |
| 4,746,643 A | 5/1988 | Buonomo et al. |
| 4,751,342 A | 6/1988 | Kimble |
| 4,764,497 A | * 8/1988 | Yuasa et al. .......... 502/235 |
| 4,902,848 A | 2/1990 | Scott |
| 4,954,653 A | 9/1990 | Bellussi et al. |
| 4,956,515 A | 9/1990 | Kolts et al. |
| 4,973,791 A | * 11/1990 | Vrieland et al. ........ 585/624 |
| 4,981,831 A | * 1/1991 | Knudsen et al. ........ 502/236 |
| 5,086,032 A | 2/1992 | Mazzocchia et al. |
| 5,162,283 A | * 11/1992 | Moini ................. 502/236 |
| 5,198,580 A | 3/1993 | Bartek et al. |
| 5,202,517 A | 4/1993 | Minet et al. |
| 5,220,092 A | * 6/1993 | Clark et al. ........... 585/661 |
| 5,227,566 A | 7/1993 | Cottrell et al. |
| 5,254,779 A | 10/1993 | Mazzocchia et al. |
| 5,434,118 A | 7/1995 | Carati et al. |
| 5,578,744 A | * 11/1996 | Carati et al. .......... 585/530 |
| 5,744,619 A | 4/1998 | Nemeth et al. |
| 5,902,918 A | * 5/1999 | Hagemeyer et al. ..... 585/440 |
| 5,935,895 A | 8/1999 | Baiker et al. |

FOREIGN PATENT DOCUMENTS

EP 397637 A1 * 11/1990
EP 403462 A1 * 12/1990

OTHER PUBLICATIONS

Stern et al., Propane Oxydehydrogenation Over Molybdate–Based Catalysts, Journal of Catalysis 167, 550–559 (1997).
Meunier et al., Oxidative Dehydrogenation of Propane Over Molybdenum–Containing Catalysts, Catalysis Today 37, 33–42 (1997).
Driscoll et al., Characterization, Activity, and Adsorption/Desorption Behavior of Alkali/Promoted Molybdate Catalysts for the Oxidative Coupling of Methane, Journal of Catalysis 147, 379–392 (1994).
Ross, Alkali Doping in Heterogeneous Catalysis, Catal. Rev.–Sci. Eng. 25(4), 591–637 (1983).
Abello et al., Selective Oxidation of Propane on MgOy–A1203–Supported Molybdenum Catalyst: Influence of Promoters, Catalysis Letters 53, 185–192 (1998).
Notari, Microporous Crystalline Titanium Silicates, Advanced in Catalysis 41, 253–333 (1996).
Stakheev et al., XPS and XAES Study of TiO2–SiO2 Mixed Oxide Systems, J. Phys. Chem. 97, 5668–5672 (1993).
Lassaletta et al., Spectroscopic Characterization of Quantum–Sized TiO2 Supported on Silica: Influence of Size and TiO2–SiO2 Interface Composition, J. Phys. Chem 99, 1484–1490 (1995).
Walters et al., An Atomic–Scale Study of the Role of Titanium in TiO2–SiO2 Sol–Gel Materials, Chemical Physical Letters 264, 539–544 (1997).
Kumar et al., Phase Transformation in Sol–Gel Titania Containing Silica, Materials Letters 38, 161–166 (1999).
Klein et al., Amorphous Microporous Titania–Silica Mixed Oxides: Preparation, Characterization, and Catalytic Redox Properties, Journal of Catalysis 163, 476–488 (1996).
Liu et al., Relationships Between Microstructure and Surface Acidity of Ti—Si Mixed Oxide Catalysts, Journal of Catalysis 149, 117–126 (1994).
Vogt et al., Preparation and Performance of a Silica–Supported V2O5 on TiO2 Catalyst for the Selective Reduction of NO With NH3, Journal of Catalysis 114, 313–320 (1988).
Rieck et al., Studies of the Interactions of H2 and CO with Pd/TiO2 and TiO2–Promoted Pd/SiO2, Journal of Catalysis 99, 262–277 (1986).
Brinkler et al., Sol–Gel Science, The Physics and Chemistry of Sol–Gel Processing, Academic Press, New York (1990).
Stern et al., J. Catal. 167, 550 (1997).

(List continued on next page.)

Primary Examiner—Walter D. Griffin
(74) Attorney, Agent, or Firm—Standley & Gilcrest LLP

(57) ABSTRACT

The present invention includes a sol-gel supported catalyst for the dehydrogenation of lower alkanes, the catalyst comprising at least one active metal and at least one promoter metal attached to a sol-gel mixed oxide support. The sol-gel mixed oxide support arises from the polymerization of at least one precursor. The active metal and the promoter metal have been attached to the sol-gel mixed oxide support by the active metal and the promoter metal having been co-precipitated with the precursor of the sol-gel mixed oxide support. The invention also includes a method of making the above mentioned catalyst and a method of using the catalyst to dehydrogenate lower alkanes to produce lower alkenes.

23 Claims, 12 Drawing Sheets

OTHER PUBLICATIONS

Meunier et al., Catal. Today 37, 33 (1997).
Driscoll et al., J. Catal. 147, 379 (1994).
Erdohelyi et al., Partial Oxidation of Ethane Over Silica–Supported Alkali Metal Molybdate Catalysts, Journal of Catalysis 135, (1992) 563–575.
Ross, Catal. Rev.–Sci. Engl. 25(4), 591 (1993).
Abello et al., Catal. Letters 53, 53 (1998).
Notari, Adv. Catal. 41, 253 (1996).
Stakheev et al., J. Phys. Chem. 97, 5668 (1993).
Lassaletta et al., J. Phys. Chem. 99, 1484 (1995).
Walters et al., Chem. Phys. Letters 264, 539 (1997).
Kumar et al., Mat. Letters 38, 161 (1999).
Klein et al., J. Catal. 163, 476 (1996).
Liu et al., J. Catal. 149, 117 (1994).
Baiker et al., Selective Catalytic Reduction of Nitric Oxide with Ammonia, Applied Catalysis, 35 (1987) 365–380.
Vogt et al., J. Catal. 114, 313 (1988).
Udomsak et al., Isobutane Dehydrogenation on Chromia/Silica–Titania Mixed Oxide and Chromia/y–Alumina Catalysts, Ind. Eng. Chem. Res. 35, 47 (1996).
Rieck et al., J. Catal. 99, 262 (1986).
Feng et al., Reactions of Propane on Modified Metal Oxides, Journal of Catalysis 136, (1992) 423–431.
Brinker et al., "Sol–Gel Science", Academic Press, New York, 1990.
Dutoit et al., Vanadia–Silica Aerogels Structure and Catalytic Properties in Selective Reductions NO by $NH_3$, Applied Catalysis B: Environment 13 (1997) 275–288.
Grabowski et al., Effect of Alkaline Promoters on Catalytic Activity of $V_2O_5/TiO_2$ and $MoO_3/TiO_2$ Catalysts in oxidative Dehydrogenation of Propane and in Isopropanol Decomposition, Applied Catalysis A: General 125 (1995) 129–144.
Wachs, Raman and IR Studies of Surface Metal Oxide Species on Oxide Supports: Supported Metal Oxide Catalysts, Catalysis Today 27 (1996) 437–455.
Wang et al., Characterization of Vanadia Sites in V–Silicalite, Vanadia–Silica Cogel, and Silica–Supported Vanadia Catalysts: X–Ray Powder Diffractions, Raman Spectroscopy, Solid–State 51V NMR, Temperature–Programmed Reduction, and Methanol Oxidation Studies, Journal of Catalysis 178, 640–648 (1998).
Wachs et al., Structure and Reactivity of Surface Vanadium Oxide Species on Oxide Supports, Applied Catalysis A: General 157 (1997) 67–90.
Blasco et al., Oxidative Dehydrogenation of Short Chain Alkanes on Supported Vanadium Oxide Catalysts, Applied Catalysis A: General 157 (1997) 117–142.

Handy et al., Porous Silica Gels and $TIO_2/SI_2$ Mixed Oxides Prepared Via the Sol–Gel Process: Characterization of Spectroscopic Techniques, Journal of Non–Crystalline Solids 143 (1992) 93–111.

Kumbhar, Nickel Supported on Titania–Silica, Preparation, Characterisation and Activity for Liquid–Phase Hydrogenation of Acetophenome, Applied Catalysis A: General, 96 (1993) 241–252.

Miller et al., Synthesis, Characterization, and Activity Studies of $V_2O_5/ZrO_2$–$SiO_2$ Catalysts, Journal of Catalysis 184, 68–76 (1999).

Gao et al., Titania–Silica as Catalysts: Molecular Structural Characteristics and Physico–Chemical Properties, Catalysis Today 51 (1999) 233–254.

Watson et al., K/Mo Catalysts Supported over Sol–Gel Silica–Titania Mixed Oxides in the Oxidative Dehydrogenation of Propane, Journal of Catalysis 190 (2000) 1–18.

Ko et al., A Studay of Acidic Titania–Silica Mixed Oxides and Their Use as Supports for Nickel Catalysts, Journal of Catalysis 105 (1987) 511–520.

Reddy et al., Synthesis of Isobutyraldehyde From Methanol and Ethanol Over Mixed Oxide Supported Vanadium Oxide Catalysts, Applied Catalysis A: General 96 (1993) L1–L5.

Dias et al., Selective Oxidation of o–xylene to Phthalic Anhydride on $V_2O_5$ Supported on $TiO_2$–Coated $SiO_2$, Catalysis Letters 43 (1997) 117–121.

Suh et al., Nickel–Alumina Aerogel Catalysts Prepared by Fast Sol–Gel Synthesis, Journal of Non–Crystalline Solids 225 (1998) 168–172.

Grunwaldt et al., Unusual Redox Properties of Bismuth in Sol–Gel Bi—Mo—Ti Mixed Oxides, Journal of Catalysis 177 (1998) 53–59.

Al–Adwani et al., Synthesis Characterization, and Catalytic Activity of Sulfided Silico–Alumino–Titanate (Si—Al—Ti) Mixed Oxides Xerogels Supported Ni—Mo Catalyst, Journal of Catalysis 177 (1998) 273–283.

Iwamoto et al., Acidity and Hydrogenation Properties of Mo—P–Alumina Catalysts Prepared by a Sol–Gel Method, Journal of Catalysis 172 (1997) 252–255.

Iwamoto et al., Genesis, Characterizations and HDS Activity of Mo—P–Alumina Based Hydrotreating Catalysts Prepared by a Sol–Gel Method, Elsevier Science B.V. (1997) 195–210.

* cited by examiner

US 6,521,808 B1

PREPARATION AND USE OF A CATALYST FOR THE OXIDATIVE DEHYDROGENATION OF LOWER ALKANES

TECHNICAL FIELD OF THE INVENTION

The present invention is in the field of dehydrogenation catalysts using a modified sol-gel/co-precipitation technique.

BACKGROUND OF THE INVENTION

Over the past 15 years, many academic and industrial research efforts have focused on the conversion of lower alkanes ($C_1$–$C_5$) to petrochemical feed stocks. These catalytic reactions include: methane partial oxidation to formaldehyde and oxidative coupling to $C_2$ hydrocarbons; ethane and propane oxidative dehydrogenation to olefins and oxygenates (acetic acid, acrolein, acrylic acid); and butane and pentane oxidative dehydrogenation to maleic and phthalic anhydrides. Thus far, there are no industrially practical operations for such applications except for the production of maleic anhydride from butane.

The research drive to develop an oxidative dehydrogenation process for propane and ethane comes from the fact that the chemical industry depends heavily on propene and other alkene feed stocks. For example, propene demand is estimated to grow 4.5% per year between 1991 and 2000. Catalytic oxidative dehydrogenation (ODH) is an attractive alternate route for the production of alkenes compared to conventional cracking and dehydrogenation processes. This is because ODH is thermodynamically favored at lower temperatures and usually does not lead to the formation of coke and smaller hydrocarbons. Recent literature has focused on selective, high surface area catalysts active below 823K that can limit the amount of carbon oxides formed. In our recent work, an observed yield of propene of 30% was obtained in the oxidative dehydrogenation of propane. This is among the highest yields ever reported for this type of reaction. Furthermore, certain formulations of the catalyst lead to little or no carbon monoxide production. These facts make this catalyst a viable option for an industrial process.

Some of the most selective oxidative dehydrogenation catalysts reported in, recent literature consist of vanadium and molybdenum compounds. In particular, promising results have been obtained when molybdate-based catalysts are promoted or supported. For example, Ni—Co—Mo, V—Nb—Mo/$TiO_2$, K—$MnMoO_4$, and $K_2MoO_4$ have shown promise in ODH and other partial oxidation reactions. The positive effect of alkali dopants (Li, Na, K, Rb, and Cs) has been discussed in many oxidation reactions and is becoming more and more applicable to different catalysts. However, the effect is still not well characterized. Alkali doping can have the effect of increasing selectivity and activity while preventing phase transformations, inhibiting sintering, and creating basic centers on the catalyst surface. Abello et al. in *Catal. Letters* 53, 53 (1998) have shown a significant increase in selectivity on Mo/MgO-$\gamma$-$Al_2O_3$ with the addition of potassium. On this catalyst, an interesting trend was noticed in catalyst activity, redox behavior, and surface acidity. Furthermore, past work from our group has shown that potassium can largely affect oxygen exchange between bulk $MnMoO_4$ catalysts and gas phase oxygen as well as adsorption/desorption behavior of the catalyst. These parameters are the most common features used to describe ODH catalysts.

As previously mentioned, the study of silica-titania mixed oxides has gained much attention because of their high activity for epoxidation reactions of olefins with hydroperoxides. It has been cited that $TiO_2$ in mixed oxides of silica and titania can be present not only as anatase, but in the form of very small domains in which the normal octahedral coordination of $TiO_2$ has changed to tetrahedral (see Notari, B., *Adv. Catal.* 41, 253 (1996)). This leads to the unique structural and chemical properties of this material. Silica-titania mixed oxide supports, through sol-gel preparations, can provide advantages that the respective single oxides cannot. These benefits include stronger metal-support interactions, hindering reduction of the active metal, and smaller particle size that leads to better dispersion and higher surface area. Silica-titania mixed oxides have been studied extensively for attributes such as acidity, porosity, Ti—O—Si connectivity, and phase separations. However, few studies have been done on their use as active metal supports.

Baiker et al. in *Appl. Catal* A 35, 365 (1987) and Vogt et al. in *J. Catal.* 114, 313 (1988) have used vanadia supported on silica-titania mixed oxides for the reduction of nitric oxide with ammonia. Baiker et al. has shown that the addition of titania causes an interaction that prevents agglomeration of surface vanadia species. Udomsak et al. in *Ind. Eng. Chem. Res.* 35, 47 (1996) have shown a significant difference in isobutane dehydrogenation activity on chromia/silica-titania catalyst with different preparation methods. Hydrogen and carbon monoxide interaction with titania promoted palladium on silica was studied by Rieck and Bell in *J. Catal.* 99, 262 (1986). Here, it was shown that TiO, species decorate the palladium, causing a notable difference in the CO adsorption behavior. Feng et al. in *J. Catal,* 136, 423 (1993) have shown the hydrogen abstracting ability of the weakly acidic silica titania mixed oxide supported palladium catalysts was the dominating factor for non-oxidative dehydrogenation of propane.

Sol-gel science is well summarized well by Brinker and Scherer in "Sol-Gel Science", Academic Press, New York, 1990, but the use of sol-gel preparations for supported metal catalysts is sparse. The use of the technology combined with active metal dispersion is limited to conventional techniques, such as wet impregnation (making the Si:Ti support first, then dispersing active components). Combining the positive effects of alkali doping and sol-gel science in a way to disperse the active component as the support network is forming has never been attempted in known literature.

Study of silica-titania mixed oxides have gained much attention because of their high activity for epoxidation reactions of olefins with hydroperoxides. Silica-titania mixed oxide supports, through sol-gel preparations, can provide advantages that the respective single oxides ($SiO_2$, $TiO_2$) cannot. Silica-titania mixed oxides have been studied extensively. However, few studies have been done on their use as active metal supports. Furthermore, catalysts containing active metals supported over Si:Ti mixed oxides have not been prepared in the manner of this invention nor do they use the same materials.

The above-cited references are hereby incorporated by reference.

SUMMARY OF THE INVENTION

The present invention includes a catalyst, a method for its preparation and a method for using the catalyst.

The present invention includes a sol-gel supported catalyst for the dehydrogenation of lower alkanes, the catalyst comprising at least one active metal and at least one promoter metal attached to a sol-gel mixed oxide support. The sol-gel mixed oxide support arising from the polymerization of at least one precursor. The active metal and the promoter metal having been attached to the sol-gel mixed oxide support by the active metal and the promoter metal having been co-precipitated with the precursor of the sol-gel mixed oxide support.

Lower alkanes, as used herein, may typically include those alkanes of $C_{(1-5)}$ carbons.

The active metal, as used herein, may be any metal adapted to bring about oxidative dehydrogenation activity and may preferably include molybdenum or vanadium. The active metal may be present in any amount that is effective and may include anywhere from 1 to 70% by weight of the finished catalyst and more particularly from 1 to 20% by weight.

The promoter metal (also called the alkali promoter), as used herein, is selected from the group consisting of alkali metals, alkaline earth metals, rare earth metals, and mixtures thereof. The promoter metal is preferably selected from metals from Group IA of the Periodic Table, in particular, the promoter metal may include alkali metals such as Li, Na, K, Rb, or Cs.

The active metal is supported over a mixed metal oxide support and may preferably include a silica-titania mixed oxide support (i.e. $SiO_2$—$TiO_2$). The support mixed metal oxide molar ratio may range from 0:1 to 1:0, with a Si:Ti ratio of 1:1 being the most preferred.

Furthermore, promoter metal loading has been on a molar basis and has ranged from 0 to above 2-alkali/active metal molar ratios.

Also included within the scope of the present invention is a method of producing a sol-gel supported catalyst. The method comprising: obtaining a sol-gel precursor solution comprising at least one silicon alkoxide and at least one titanium alkoxide in a solution, adding to the sol-gel precursor solution at least one active metal-containing precursor in aqueous solution and at least one promoter metal-containing precursor in solution; and allowing the silicon alkoxide and the titanium alkoxide to become polymerized to form a sol-gel while allowing the active metal-containing precursor and the promoter metal-containing precursor to precipitate.

Active metal-containing precursors, as used herein, may be selected from the group consisting of ammonium heptamolybdate, molybdenum isopropoxide, molybdic acid, silicomolybdic acid, molybdenum chloride, molybdenum oxide, vanadium chloride, vanadium oxyalkoxides, vanadium acetylacetonate, vanadium pentoxide, vanadium acetate, pure V and Mo powders and other molybdenum or vanadium precursors.

Promoter metal-containing precursors, as used herein, may be selected from the group consisting of carbonates, nitrates, hydroxides, chlorides and molybdates of alkali, alkaline earth and rare earth metals (i.e. $X_2MoO_4$ where X is any of the above-mentioned metals).

The catalyst may be prepared in a solvent. The solvent may be any solvent that can dissolve titanium or silicon alkoxides. The solvent may be selected from alcohol, hexane, benzene or other polar-aprotic solvents to name a few. If alcohol is used, it may comprise pure or mixed alcohols selected from the group consisting of methanol, ethanol, propanol, iso-propanol, and butanol.

Finally, the present invention includes a method of dehydrating lower alkanes to produce lower alkenes using a catalyst. The method comprising the steps: (a) obtaining a sol-gel supported catalyst, the catalyst comprising at least one active metal and at least one promoter metal attached to a sol-gel mixed oxide support. The sol-gel mixed oxide support arising from the polymerization of at least one precursor thereof, the active metal and the promoter metal having been attached to the sol-gel mixed oxide support by the active metal and the promoter metal having been co-precipitated with the precursor of the sol-gel mixed oxide support; and (b) bringing into contact with the catalyst at least one lower alkane for sufficient time and at sufficient temperature so as to allow the lower alkane to be dehydrogenated.

The precursor of the sol-gel mixed oxide support, as used herein, may be any liquid alkoxide compound and is preferably silicon and titanium alkoxides. These include $Si(OR)_4$ and $Ti(OR)_4$, where R can be $CH_3$, $C_2H_5$, linear $C_3H_7$, branched $C_3H_7$ (isopropyl) or $C_4H_9$.

DETAILED DESCRIPTION OF THE PREFERRED EMBODIMENT

Figure 1:
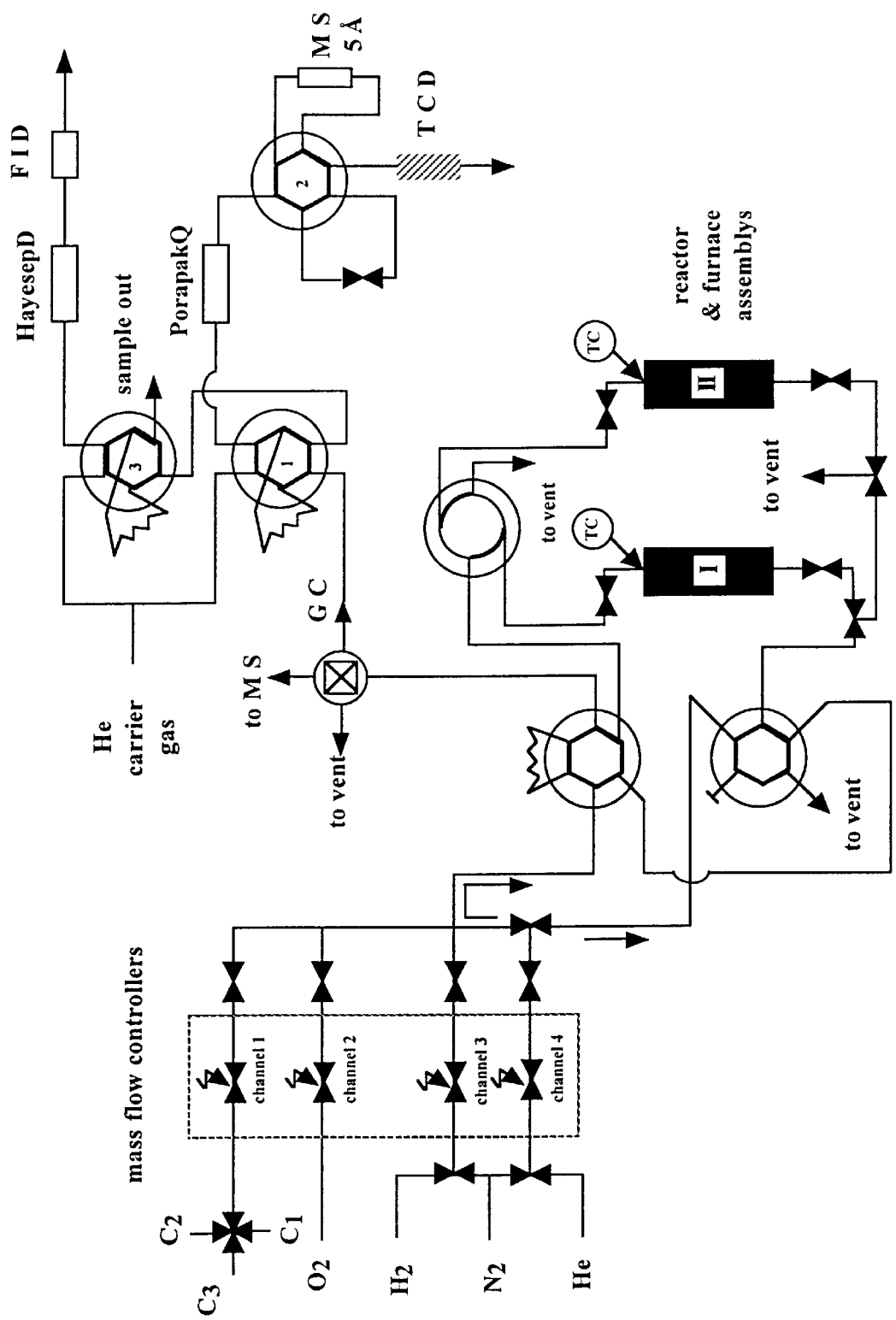
FIG. 1 shows a lower alkane partial oxidation/oxidative dehydrogenation reactor system, in accordance with one embodiment of the present invention.

In accordance with the foregoing summary, the following presents a detailed description of the preferred embodiment of the invention that is currently considered to be the best mode.

The preferred method of preparation of the catalyst is as follows. This method takes advantage of sol-gel chemistry, or in other words, inorganic polymerization. During slow addition of water (hydrolysis), the alkyl group leaves and forms an alcohol by nucleophilic addition of water. The next three types of reactions are condensation reactions in which the support structure forms; alcoxolation, oxolation, and olation. The reaction type the alkoxide precursors use to form depends on the charge of the metal, the leaving group, and the type of solvent used. There are many parameters that affect the final structure of the sol-gel prepared silica-titania oxide, including, the charge on metal, the coordination chemistry, the composition, the electronegativity, the pH, what alkoxy groups are used, the water/precursor ratio, the rate at which the water is added, the addition of catalyzing agent, the concentration, the solvent employed, the temperature, and the drying /aging methods. As they pertain to surface area, final catalyst activity, and selectivity several parameter have been studied. Important information has been obtained regarding hydrolysis conditions, solvent effects, pH control, and drying conditions that have been used in further catalyst preparations.

One of the features believed to be unique in the preparation method of the present invention comes from the addition of the active metal and promoter metal. Aqueous solutions of active metal precursor and promoter metal precursors are contained in the hydrolyzing water and are added slowly to the solution containing Si and Ti alkoxide precursors.

For instance, alkali molybdates precipitate in the solution as Si and Ti alkoxides and are hydrolyzed to form Si—O—Si, Ti—O—Ti, and Ti—O—Si networks. This preparation method has been termed a modified, "one-pot" sol-gel/co-precipitation technique. Some of the advantages of this preparation method may include stronger metal-support interactions, hindering reduction of the active metal, and smaller particle size that leads to better dispersion and higher surface area.

The catalyst may be used for the oxidative dehydrogenation of propane in a catalytic, gas-phase reaction in which the feed consists of propane/oxygen/nitrogen at varying low rates and propane/oxygen molar ratios. The concentration of the feed stream should be maintained outside the flammability limits of propane-oxygen-nitrogen mixtures. The reaction temperature may preferably range from 300 to 550° C. The main products of this type of dehydrogenation reaction are propene, ethylene, carbon dioxide, carbon monoxide, and water. Acrolein was the only oxygenated product observed, and when observed, was at the ppm level.

EXAMPLES

Catalysts may be prepared using a modified sol-gel, co-precipitation technique. The method that may be used involves the reaction of metal alkoxide precursors in an alcohol solvent when contacted with water. During hydrolysis, the alkyl group leaves and forms an alcohol by nucleophilic addition of water. The next three types of reactions are condensation reactions; alcoxolation, oxolation, and olation. The type of reaction that the alkoxide precursors condense by depends on the charge of the metal, the leaving group, and the type of solvent used. There are many parameters that affect the final structure of the silica-titania that is prepared by the sol-gel method. These include the charge on metal, the coordination chemistry, the composition, the electronegativity, the pH, the number and type of alkoxy groups, the water/precursor ratio, the addition of catalyzing agent, the concentration, the solvent used, the temperature, and the drying/aging methods.

Ammonium heptamolybdate, (AHM) (Mallinkrodt) and KOH (Fisher) were used for molybdenum and potassium precursors respectively. For silica-titania mixed oxides, tetraethylorthosilicate (TEOS) (Aldrich) and titanium(IV) isopropoxide (TIPO) (Aldrich) were used.

The solvent was isopropyl alcohol. In this modified sol-gel method, calculated amounts of the silica and titania alkoxide precursors were placed in 100 mL of solvent to yield, after calcination, $SiO_2$—$TiO_2$ mixed oxides with the desired Si:Ti molar ratio. This solution was left stirring while an aqueous solution containing the necessary amount of AHM (10% Mo loading) was then added drop-wise with a syringe pump. The aqueous solution added contained the stoichiometric amount of water necessary to hydrolyze all of the alkoxide precursors. The aqueous solution was added at a rate of 0.5 $cm^3$/minutes for all catalysts with one exception. For the catalyst prepared with fast addition, the aqueous solution was added at a rate of 2 $cm^3$/minutes. For catalysts containing potassium, KOH was added to the aqueous solution to give the desired K/Mo molar ratio. For catalysts denoted as pre-hydrolyzed, the stoichiometric amount of water necessary to hydrolyze the entire silica precursor was added to the silica precursor first and stirred for 15 minutes. Then, the titania precursor was added followed by the addition of the aqueous solution of potassium and molybdenum. For acidic and basic preparations, the effective pH of the alcohol solution was maintained at pH=3 (acidic) and pH=11 (basic) during preparation using $HNO_3$ and $NH_4OH$ respectively. Resulting gels were stirred for an additional 15 minutes after all of the aqueous solution had been added and dried at room temperature for less than 3 hours. They were then placed into an oven at 110° C. for overnight drying and solvent removal. After drying, the catalysts were ground to a fine powder and calcined under oxygen at 550° C. for 5 hours. This method is referred to as a "one-pot" sol-gel/co-precipitation because as the silica and titania precursors are hydrolyzed and precipitate out of solution, potassium molybdate species, that are insoluble in alcohol, also precipitate.

Synthesized catalysts are listed in Table 1 below. Catalysts numbered 1 through 7 are a series of molybdate catalysts with increasing K/Mo molar ratio at constant (10 weight %) loading of Mo and a Si:Ti molar ratio of 1. Catalysts 8 through 11 were prepared keeping K/Mo constant at 2 and varying the silica and titania content. Since TEOS hydrolyzes much slower than TIPO a series pre-hydrolyzed catalysts were also prepared. Catalysts 12 through 15 were synthesized using different hydrolysis methods (pre-hydrolysis of silica precursor, fast or slow addition, and acidic or basic conditions). Catalysts 16 and 17 refer to a bare-silica titania support and a potassium-doped silica titania support, respectively.

BET surface area measurement and nitrogen adsorption-desorption isotherms were recorded using a Micrometrics AccuSorb 2100E instrument. X-ray diffraction was performed with a Scintag PAD-V diffractometer using, Cu—Kα radiation. Raman spectra were recorded with a Dilor spectrometer using the 514.5 nm line of an Innova 300 Ar Laser. Spectra were taken in the range 200–1800 $cm^{-1}$ in 180° back-scattering mode with a Spectrum One CCD detector.

TABLE 1

Sol-gel catalysts and supports

| # | Composition | Preparation | Surface Area (m²/g) |
|---|---|---|---|
| 1 | 10% Mo/Si:Ti 1:1 | sol-gel | 229 |
| 2 | 10% (K/Mo = 0.07)/Si:Ti 1:1 | co-precip., sol-gel | 136 |
| 3 | 10% (K/Mo = 0.14)/Si:Ti 1:1 | co-precip., sol-gel | 121 |
| 4 | 10% (K/Mo = 0.3)/Si:Ti 1:1 | co-precip., sol-gel | 166 |
| 5 | 10% (K/Mo = 0.6)/Si:Ti 1:1 | co-precip., sol-gel | 65 |
| 6 | 10% (K/Mo = 1)/Si:Ti 1:1 | co-precip., sol-gel | 17 |
| 7 | 10% (K/Mo = 2)/Si:Ti 1:1 | co-precip., sol-gel | 106 |
| 8 | 10% (K/Mo = 2)/SiO₂ | co-precip., sol-gel | 156 |
| 9 | 10% (K/Mo = 2)/TiO₂ | co-precip., sol-gel | 43 |
| 10 | 10% (K/Mo = 2)/Si:Ti 2:1 | co-precip., sol-gel | 75 |
| 11 | 10% (K/Mo = 2)/Si:Ti 1:2 | co-precip., sol-gel | 17 |
| 12 | 10% (K/Mo = 2)/Si:Ti 1:1 | acidic prehydrolyzed sol-gel | 271 |
| 13 | 10% (K/Mo = 2)/Si:Ti 1:1 | fast prehydrolyzed sol-gel | 149 |
| 14 | 10% (K/Mo = 2)/Si:Ti 1:1 | prehydrolyzed sol-gel | 178 |
| 15 | 10% (K/Mo = 2)/Si:Ti 1:1 | basic prehydrolyzed sol-gel | 179 |
| 16 | Si:Ti Support only | sol-gel | 320 |
| 17 | K doped Si:Ti support | sol-gel KOH (for K/Mo = 2) | 380 |

Temperature programmed reduction (TPR) of catalysts was performed using a laboratory-made gas flow system described in detail elsewhere. Catalyst samples (100 mg) were placed in a ¼-in.-i.d. U-tube quartz reactor flow at 550° C. for thirty minutes followed by cooling to room temperature under nitrogen. The reduction was performed with 10% hydrogen in nitrogen (25 cm³/minutes). The thermal conductivity detector (TCD) was operated in differential mode and the signal transferred to a data acquisition computer. The outlet of the reactor was passed through a column of silica gel to remove moisture formed during the reduction. The temperature program was as follows: 10 minutes at room temperature, 10°/minutes ramp rate to 850° C., and holding at 850° C. for 10 minutes.

X-ray photoelectron spectroscopy (XPS) of catalysts was performed with Physical Electronics/Perkin Elmer (model 550) ESCA/Auger Spectrometer operated at 15 kV, 20 mA, and using Mg—Kα radiation. Spectra were corrected using the C 1 s signal, located at 284.6 eV. Relative percentages of $K_2MoO_4$ and $MoO_3$ in the samples were calculated using the integrals of the de-convoluted Mo 3d spectra. The de-convolution of Mo 3d spectra was accomplished using linked lets of equal FWHM, an intensity ratio of 2/3, and a splitting of 3.15 eV.

Diffuse Reflectance Infrared Fourier Transform Spectroscopy (DRIFTS) of the catalysts was performed using a Bruker IFS66 equipped with a DTGS detector and a KBr beamsplitter. Catalysts were placed in a sample cup inside a Spectratech diffuse reflectance cell equipped with KBr windows and a thermocouple mount that allowed direct measurement of the surface temperature. Room temperature spectra for each catalyst were averaged over 1000 scans in the mid-IR range (400–4000 cm⁻¹) to a nominal 2 cm⁻¹ resolution. Prior to collecting spectrum, catalysts were pretreated under 10% oxygen in helium for thirty minutes at 400° C. surface, temperature to remove adsorbed water and carbon dioxide. For $NH_3$ adsorption experiments, background was taken under helium at room temperature. Following background measurement, $NH_3$ adsorption (0.5%$NH_3$/He) was performed for 1 hour. Spectra were taken after evacuation for thirty minutes under helium. For in situ reaction spectra, background spectrum was taken at room temperature and with the sample surface temperature at 450° C. Gas phase spectra were taken at 450° C. The spectrum was taken after 15 minutes to 1 h of exposure to reaction mixture (%$N_2/C_3/O_2$:61/26/13) afterwards a spectrum was taken once the reaction chamber was quenched to room temperature under nitrogen flow.

Propane Temperature Programmed Desorption (TPD) of catalysts was performed using the same laboratory-made gas flow system described for TPR experiments. Catalyst samples (100 mg) were placed in a ¼-in.-i.d. U-tube quartz reactor and pretreated under oxygen flow at 550° C. for thirty minutes followed by cooling to room temperature under helium. Samples were flushed with helium for 1 h followed by 1 h of propane adsorption. After adsorption, desorbed species were followed by a HP5890GC-MS under helium carrier gas. For these studies, the G.C. columns were replaced by an empty capillary column. The mass spectrometer was equipped with a quadrupole mass analyzer that allows tracking of up to 20 mass-to-charge ratios (m/z) simultaneously in the selected ion mode. Identification of species with equal m/z ratios was accomplished by following characteristic mass fragments of the species. The temperature program was as follows: 10 minutes at room temperature, 10°/minutes ramp rate to 700° C., and holding at 700° C. for 20 minutes.

Steady state reaction experiments were carried out in a fixed-bed, quartz reactor, operated at ambient pressure. The reactor system, shown in FIG. 1, is such that gaseous feed may be directed through ⅛-in. stainless steel lines into the reactor and furnace assemblies. An HP 5890 series II gas chromatograph equipped with FID and TCD detectors performed separations and analysis of reaction products online. Separations of hydrocarbon and inorganic species were performed using three columns: (1) Hayesep D (8-ft.×⅛-in.) (2) Porapak Q (6-ft-×⅛-in.) and (3) molecular sieve 5 Å (6-ft.×⅛-in.). Catalyst samples, ranging from 0.1 g to 1.5 g, were held in place by a quartz frit. The dead volume of the quartz microreactor was filled with quartz wool and/or ceramic beads to minimize effects from any homogeneous reaction/surface-assisted gas phase reaction and to provide a short residence time for propene formed. Reaction temperatures ranged from 723° K to 823° K. The quartz reactor, both empty and filled with quartz wool/ceramic beads, showed no activity up to 823° K. The feed consisted of propane/oxygen/ nitrogen at flows between 20–200, usually at 25 cm³/ minutes. The amount of nitrogen was varied for some runs. However, the propane/oxygen molar ratio was held constant at 2. The main products of the dehydrogenation reaction were propene, ethylene, carbon dioxide, carbon monoxide, and water. Acrolein was the only oxygenated product observed, and when observed, was at the ppm level. The product distributions maintained a carbon balance of 100% (+/−5%). Conversion is defined as the moles of carbon converted divided by the moles of carbon present in the feed. Selectivity is defined as the moles of carbon in the product divided by the moles of carbon reacted.

Molybdate catalysts show a general decrease in surface area with increasing amounts of potassium added. The catalyst with the K/Mo ratio of 2, however, is somewhat outside this trend. Furthermore, all catalysts containing potassium exhibited lower surface area than the "molybdenum only" catalyst. Comparing catalysts of different Si:Ti contents, it is seen that the highest surface area is achieved with a silica-titania molar ratio 1:1. Pre-hydrolyzed catalysts all show higher surface areas than the catalyst prepared using stoichiometric hydrolysis of both precursors. The effect of potassium on the support is shown to increase the surface area from 320 to 380 m²/g.

The nitrogen adsorption-desorption isotherm of the Si:Ti 1:1 indicated a micro to meso porous structure. The pore size distribution was calculated using the desorption isotherm. This yielded an average pore diameter of 2.1 nm and a pore volume of 0.34 cm$^3$/g.

X-ray diffraction of the Si:Ti 1:1 support yielded a pattern typical of a silica titania sample. One broad peak with center located at a d spacing of 3.59 was observed, which is the most intense diffraction line from anatase structure. A broad peak is indicative of a finely dispersed, small x-ray particulate anatase structure supported over amorphous silica. With the addition of molybdenum and potassium species, this band becomes less narrower. The presence of potassium doping also has an effect on the width of this line, making it narrower with increasing K/Mo ratio. This suggests a change in the dispersion and segregation of titania in the Si:Ti matrix. No molybdenum species can be detected in the 10%(K/Mo) loaded Si:Ti 1:1 catalysts. This indicates that molybdena species are more finely dispersed on these mixed oxide supports than on silica or titania alone. Although quite weak, the two most intense peaks from crystalline molybdenum oxide become noticeable when Mo loading level is increased to 20%.

Figure 2:
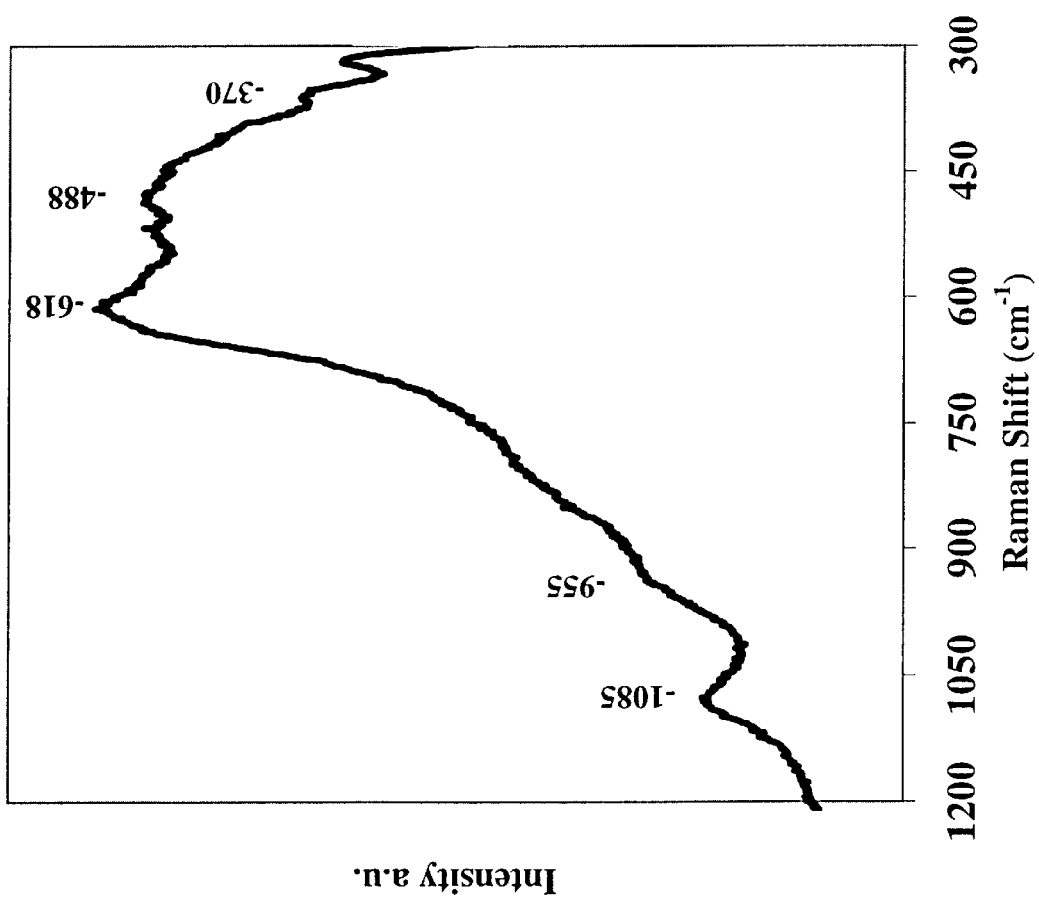
FIG. 2 shows Raman spectra of Si:Ti 1:1 support, in accordance with one embodiment of the present invention.
Figure 3:
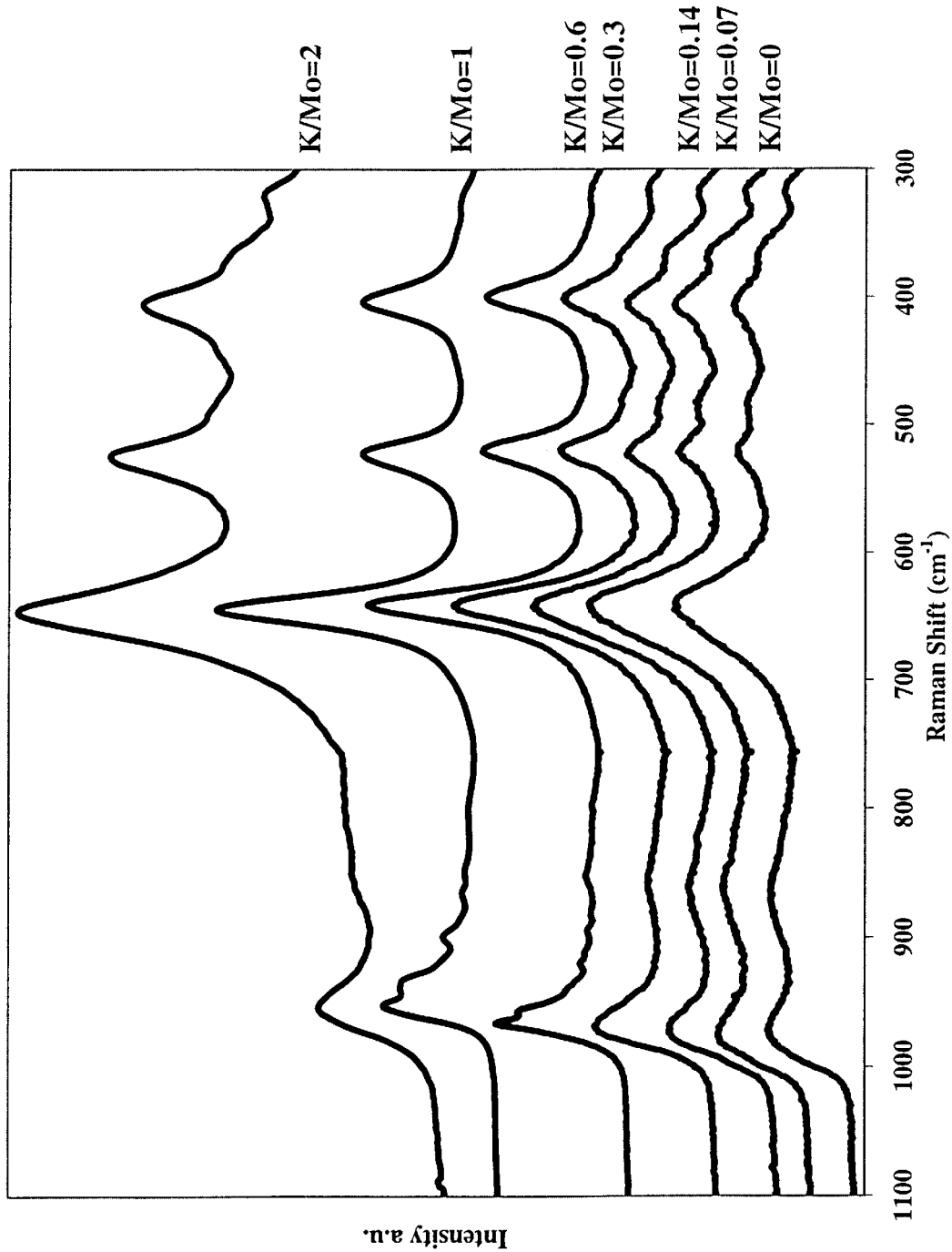
FIG. 3 shows Raman spectra of 10% (K/Mo)/Si:Ti 1:1 catalysts, in accordance with one embodiment of the present invention.

Raman spectra of the Si:Ti 1:1 support are shown in FIG. 2. The bands associated with anatase structure are shifted to lower wavenumbers than that of pure anatase and appear at 618, 488, and 370 cm$^{-1}$. The shoulder at 955 cm$^{-1}$ provides some evidence for the Si—O—Ti connectivity as reported in the literature. A second band that is associated with the SI—O—Ti bond is at 1100 cm$^{-1}$. However, this band overlaps with the asymmetric Si—O—Si stretching vibration of 1070 cm$^{-1}$ and is difficult to resolve. Raman Spectra of catalysts with different K/Mo ratios are presented in FIG. 3. Present in the spectra are the 3 bands associated with anatase at ~643, ~523, and ~404 cm$^{-1}$. These bands are shifted to lower wavenumbers than those of pure anatase and seen to grow in intensity with increasing K/Mo ratio. An important feature of these spectra is that there is little or no evidence of crystalline MoO$_3$ since the most intense band characteristic of Mo—O—Mo stretching vibrations in MoO$_3$ is not present, except as a very weak band on the catalyst with K/Mo=0.6. The bands associated with isolated terminal Mo=O stretching vibrations are visible in the 970–999 cm$^{-1}$ region. Broad bands arising from surface-coordinated Mo—O—Mo vibrations are located around 850 cm$^{-1}$. For catalysts K/Mo=0.6 and 1, there is evidence for higher crystallinity of potassium molybdate species (K$_2$MoO$_4$, K$_2$Mo$_2$O$_7$) indicated by sharper bands around 900–950 cm$^{-1}$.

Molybdenum 3d$_{5/2}$ binding energies of catalysts K/Mo supported catalysts are presented in Table 2 below. In potassium containing catalysts, molybdenum may exists in two distinct environments, one that corresponds to a MoO$_3$ matrix and the other to a K$_2$MoO$_4$ matrix. Binding energies of bulk MoO$_3$ and K$_2$MoO$_4$ are presented for comparison. When on a Si:Ti 1:1 support, our work has shown that Mo 3d binding energies shift to a lower value when compared to bulk MoO$_3$. The Mo3d$_{5/2}$ peak for the K/Mo=0.6 shows the nearest binding energy to that of bulk MoO$_3$ possibly indicating the presence of three-dimensional MoO$_3$ regions on this catalyst. The percentages of molybdenum in the MoO$_3$ matrix, calculated using the deconvoluted peak areas, closely match the "as prepared" compositions. It appears that all of the potassium added to these catalysts exists in a K$_2$MoO$_4$ type matrix. Furthermore, K 2p$_{3/2}$ spectra show one peak at an average location of 292.5eV corresponding to that of K$_2$MoO$_4$.

TABLE 2

Mo 3d$_{5/2}$ Binding Energies of Si:Ti 1:1 Supported K/Mo Catalysts

| Catalyst | 1st Mo 3d$_{5/2}$ | 2nd Mo 3d$_{5/2}$ |
|---|---|---|
| MoO$_3$ | 233.4 | — |
| 10% Mo/Si:Ti 1:1 | 232.4 | 231.7 |
| 10% (K/Mo = 0.3)/Si:Ti 1:1 | 232.6 | 231.2 |
| 10% (K/Mo = 0.6)/Si:Ti 1:1 | 233.2 | 232.0 |
| 10% (K/Mo = 2)/Si:Ti 1:1 | 232.3 | 231.6 |
| K$_2$MoO$_4$ | — | 231.8 |
|  | % MoO$_3$ - XPS | % MoO$_3$ - as prepared |
| 10% (K/Mo = 0.3)/Si:Ti 1:1 | 83 | 85 |
| 10% (K/Mo = 0.6)/Si:Ti 1:1 | 74 | 70 |
| 10% (K/Mo = 2)/Si:Ti 1:1 | 5 | 0 |

Figure 4:
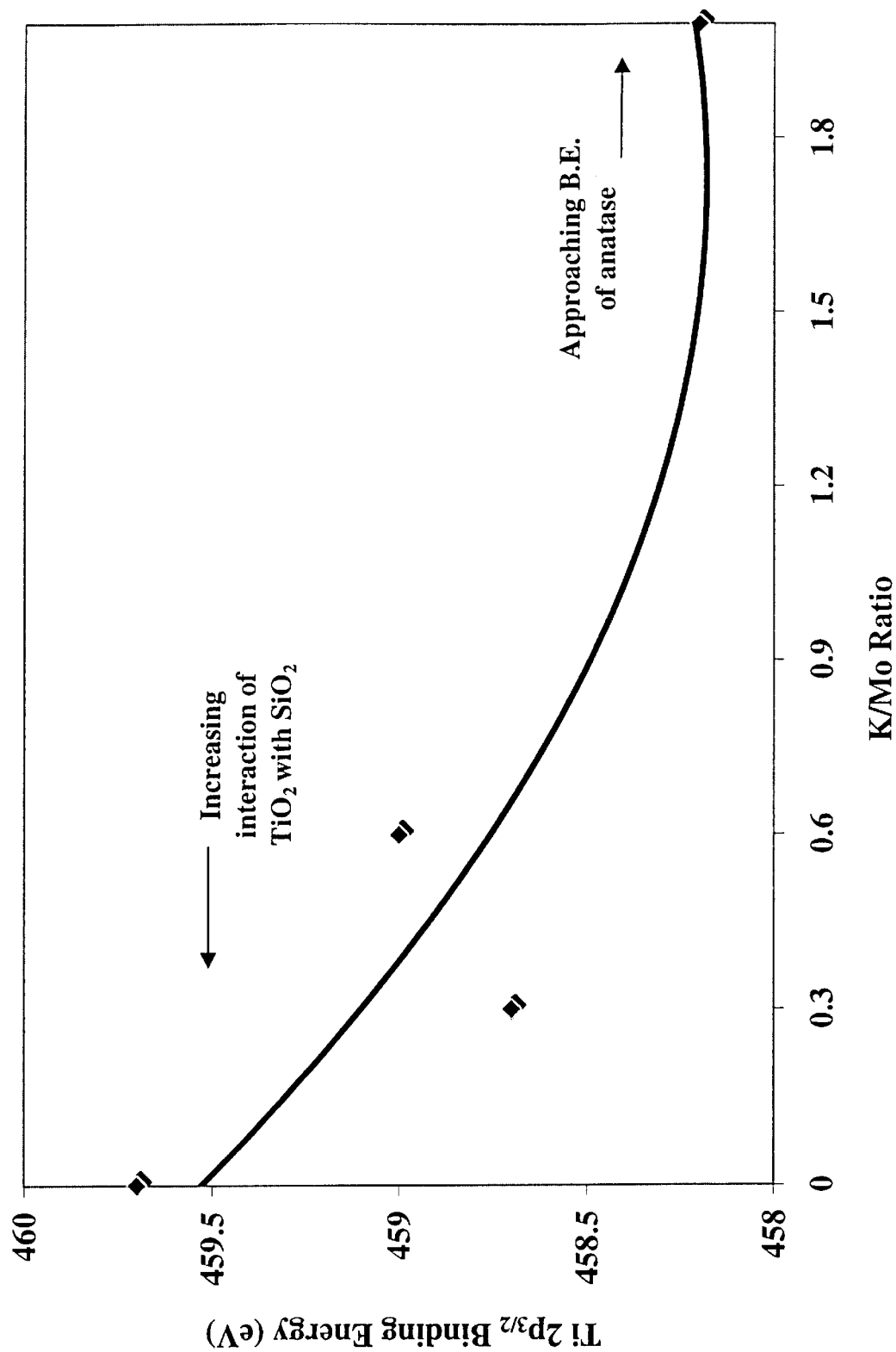
FIG. 4 shows Titania $2p_{3/2}$ binding energies for 10% (K/Mo)/Si:Ti 1:1 catalysts, in accordance with one embodiment of the present invention.

To study the change in the nature of the support with K/Mo ratio, Ti 2p$_{3/2}$ XPS were taken for catalysts with K/Mo=0, 0.3, 0.6 and 2. The variation of Ti 2p$_{3/2}$ binding energies with increasing K/Mo ratio is presented in FIG. 4. Here, the Ti 2p$_{3/2}$ binding energy is seen to shift to lower values with the addition of potassium. The binding energy for the K/Mo=0 catalyst appears at 459.7 eV indicating that titania is closely interacting with silica and in a state of very small anatase domains. The peaks shift to lower binding energies with increasing K/Mo ratios, reaching 458.2 eV for the K/Mo=2 catalyst. The Ti 2p$_{3/2}$ binding energy of pure anatase is around 458.0 eV.

Figure 5:
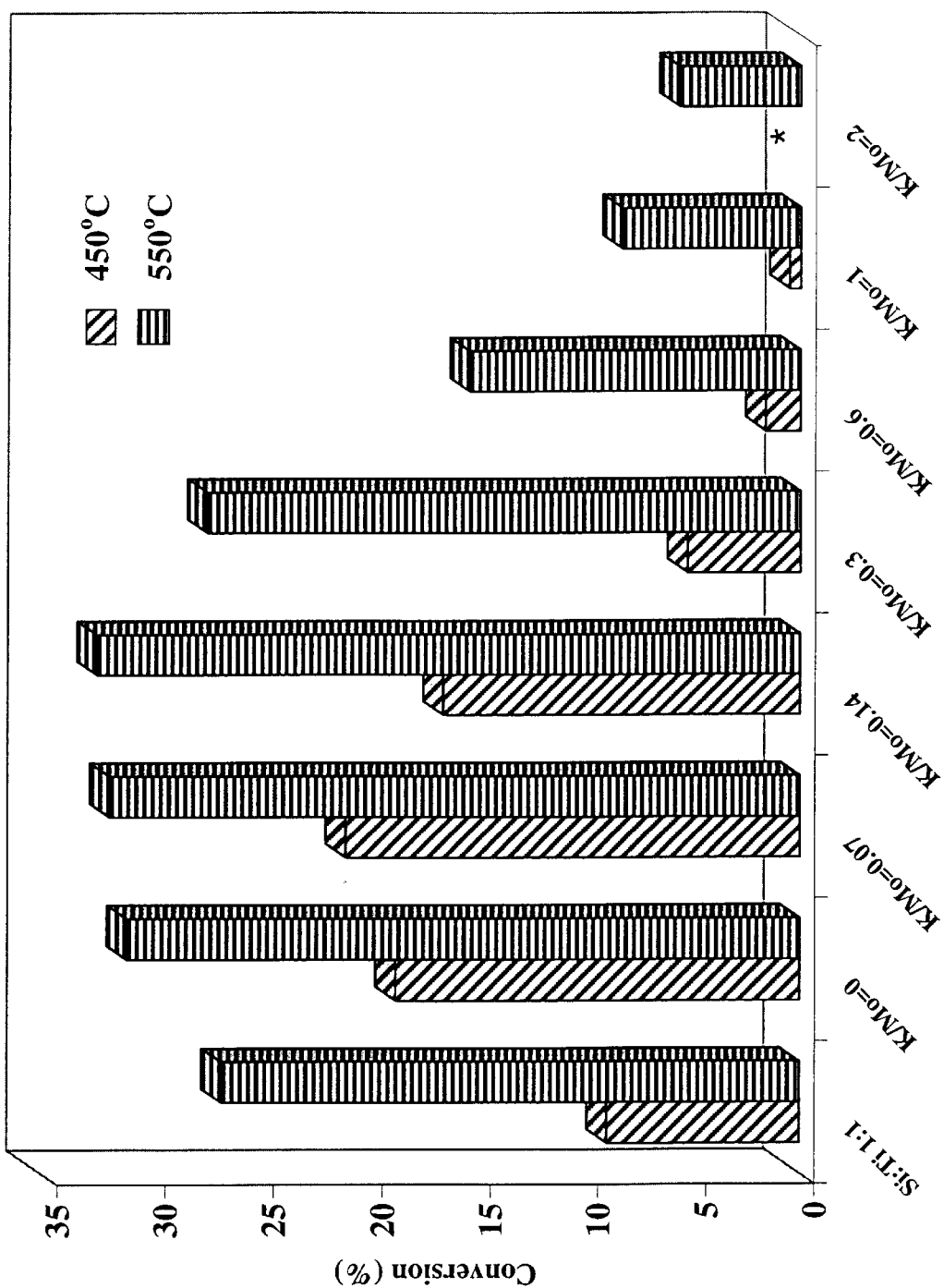
FIG. 5 shows the variation of the conversion of propane for 10%Mo/Si:Ti 1:1 catalysts with different K/Mo ratios, equal surface area reactions ($65m^2$), $\%N_2/C_3/O_2$:61%/26%/13%, 25 cc/min, in accordance with one embodiment of the present invention.

Catalysts with K/Mo ratios ranging from 0 to 2 as well as the bare Si:Ti 1:1 support, were tested in the ODH reaction using equal surface area loading (65 m$^2$) in the reactor and at temperatures of 450° C. and 550° C. The feed percentages for these experiments were N$_2$/C$_3$H$_8$/O$_2$:61%/26%/13%. Variation of propane conversion with K/Mo ratio for these equal surface area tests is presented in FIG. 5. At 450° C., conversion goes through a broad maximum reaching about 21% at K/Mo=0.07 and falls to zero at K/Mo=2. At 550° C., variation of conversion shows a similar same trend, but this time, reaching a maximum of about 33%. The Si:Ti support exhibits a higher conversion than catalysts with K/Mo=0.6 and above. Table 3 summarizes the product distribution obtained in these experiments. The yield of propylene, which is the major reaction product, mimics the trend observed for conversion, showing a broad maximum with increasing K/Mo ratio. The yield of propylene drops rather drastically at K/Mo ratios higher than 0.6. The support shows fairly high activity compared to high K/Mo-ratio catalysts. The yields of C$_2$H$_4$, C$_2$H$_6$, and CH$_4$ are all lower than 1%. At the low K/Mo ratios, the CO yield is higher than the CO$_2$ yield, but CO yield drops very rapidly with increasing K/Mo ratio.

TABLE 3

Reaction Comparison for 10% Mo/Si:Ti 1:1 Catalysts With Different K/Mo Ratios

|  | Yield | | | | | |
| --- | --- | --- | --- | --- | --- | --- |
|  | $C_3H_6$(%) | $CO_2$(%) | CO(%) | $C_2H_4$(%) | $CH_4$(%) | $C_2H_6$(%) |
| Si:Ti 1:1 | | | | | | |
| T (?C)-450 | 6.9 | 1.2 | 0.7 | 0.1 | 0.0 | 0.0 |
| T (?C)-550 | 18.9 | 3.6 | 3.6 | 0.5 | 0.2 | 0.0 |
| 10%(Mo)/Si:Ti 1:1 | | | | | | |
| T (?C)-450 | 11.4 | 2.3 | 4.9 | 0.0 | 0.1 | 0.0 |
| T (?C)-550 | 20.0 | 3.1 | 6.7 | 0.4 | 0.8 | 0.0 |
| 10%(K/Mo = 0.07)/Si:Ti 1:1 | | | | | | |
| T (?C)-450 | 13.9 | 2.3 | 4.8 | 0.0 | 0.0 | 0.0 |
| T (?C)-550 | 21.2 | 3.4 | 6.0 | 0.4 | 0.8 | 0.0 |
| 10%(K/Mo = 0.14)/Si:Ti 1:1 | | | | | | |
| T (?C)-450 | 11.3 | 1.8 | 3.4 | 0.0 | 0.0 | 0.0 |
| T (?C)-550 | 21.4 | 4.1 | 5.6 | 0.0 | 1.3 | 0.0 |
| 10%(K/Mo =0.3)/Si:Ti 1:1 | | | | | | |
| T (?C)-450 | 5.0 | 0.2 | 0.0 | 0.0 | 0.0 | 0.0 |
| T (?C)-550 | 19.9 | 3.9 | 2.9 | 0.4 | 0.4 | 0.0 |
| 10%(K/Mo =0.6)/Si:Ti 1:1 | | | | | | |
| T (?C)-450 | 1.4 | 0.2 | 0.0 | 0.0 | 0.0 | 0.0 |
| T (?C)-550 | 11.5 | 2.5 | 0.6 | 0.6 | 0.0 | 0.1 |
| 10%(K/Mo = 1)/Si:Ti 1:1 | | | | | | |
| T (?C)-450 | 0.5 | 0.0 | 0.0 | 0.0 | 0.0 | 0.0 |
| T (?C)-550 | 7.2 | 0.6 | 0.0 | 0.3 | 0.2 | 0.0 |
| 10%(K/Mo = 2)/Si:Ti 1:1 | | | | | | |
| T (?C)-450 | | | no conversion | | | |
| T (?C)-550 | 4.8 | 0.6 | 0.0 | 0.1 | 0.1 | 0.0 |

Conditions: equal surface area reactions (65 m$^2$), % $N_2/C_3/O_2$: 61%/26%/13%, 25 cc/min.

Figure 6:
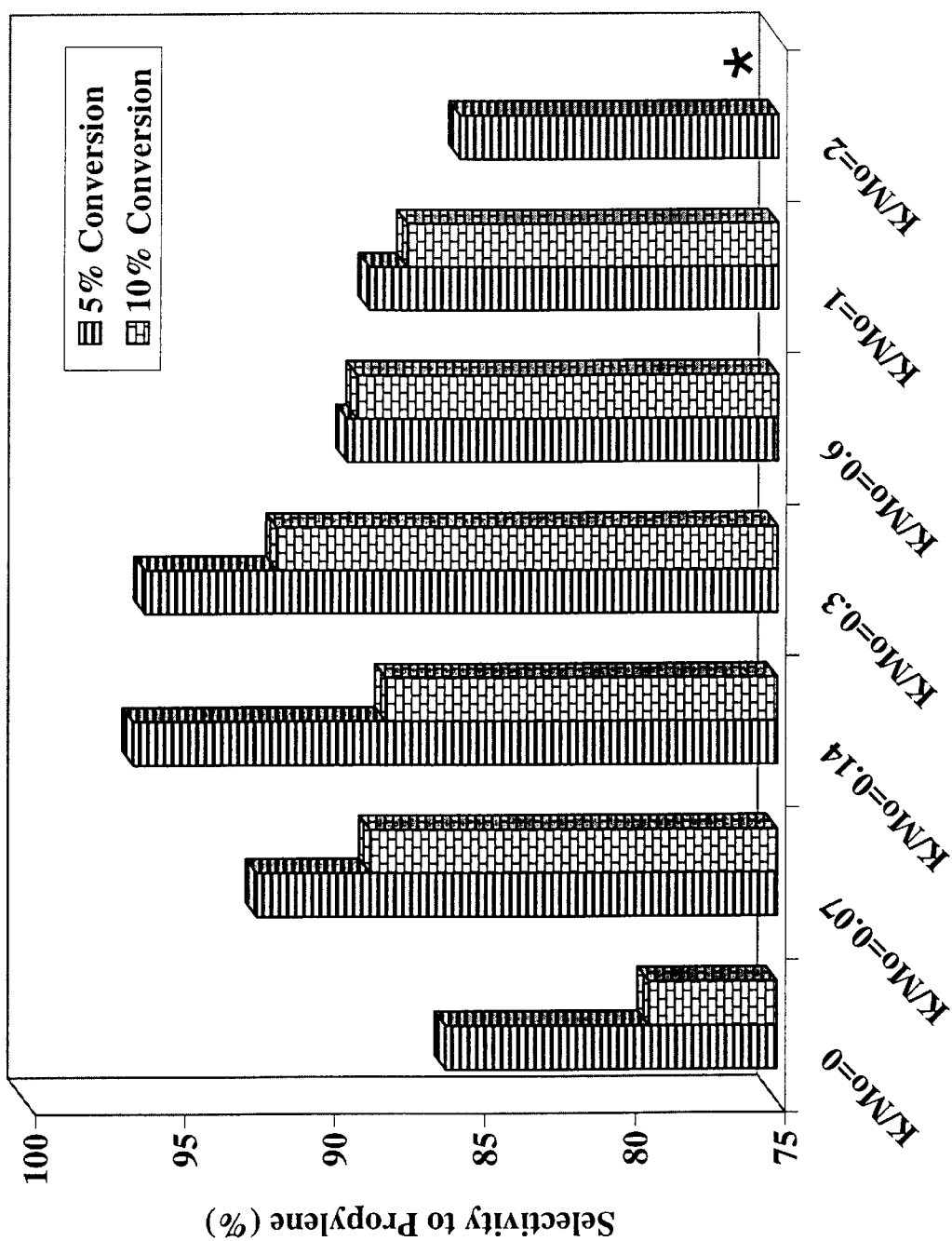
FIG. 6 shows the selectivity to propylene for 10%(K/Mo)/Si:Ti 1:1 catalysts at equal propane conversion (~5% and ~10%), 450° C., $\%N_2/C_3/O_2$:61%/26%/13%, 25 cc/min. (*-did not reach 10% Conversion), in accordance with one embodiment of the present invention.

To better compare the selectivity of these catalysts, a series experiments were performed at 450° C. keeping the propane conversion constant at 5% and at 10%. Equal conversion levels were achieved by changing the mass of catalyst loaded. The feed concentrations were the same as that of the equal surface area experiments. FIG. 6 shows the variation of propylene selectivities with K/Mo ratio at 5% and 10% conversion levels. The propylene yield goes through a relatively sharp maximum reaching yield levels of about 96% and 92% for 5% and 10% conversion, respectively. Table 4 shows the overall product distribution for the equal-conversion experiments. It is seen that the carbon monoxide selectivity decreases with the increasing K loading, dropping to zero at K/Mo ratios 0.6 and above. While CO selectivity drops to zero at these higher K/Mo ratios, we begin to see formation of ethylene and methane.

The need for high yield catalysts is one of the most important considerations for using this process in propylene production. The previously mentioned reaction results were obtained with concentrated feed mixtures ($N_2/C_3H_8/O_2$ 61%/26%/13%) to provide a higher propylene concentration in the

TABLE 4

Reaction Comparison for 10%(K/Mo)/Si:Ti 1:1 Catalysts With Different K/Mo Ratios at Equal Propane Conversion

|  | Selectivity | | | | | |
| --- | --- | --- | --- | --- | --- | --- |
|  | $C_3H_6$(%) | $CO_2$(%) | CO(%) | $C_2H_4$(%) | $CH_4$(%) | $C_2H_6$(%) |
| ~5% Propane Conversion | | | | | | |
| 10%(Mo)/Si:Ti 1:1 | 86.0 | 5.6 | 8.4 | 0.1 | 0.0 | 0.0 |
| 10%(K/Mo = 0.07)/Si:Ti 1:1 | 92.3 | 5.5 | 2.2 | 0.1 | 0.0 | 0.0 |
| 10%(K/Mo = 0.14)/Si:Ti 1:1 | 96.5 | 3.2 | 0.3 | 0.1 | 0.0 | 0.0 |
| 10%(K/Mo = 0.3)/Si:Ti 1:1 | 96.1 | 3.2 | 0.5 | 0.1 | 0.1 | 0.0 |
| 10%(K/Mo = 0.6)/Si:Ti 1:1 | 89.3 | 10.2 | 0.0 | 0.5 | 0.0 | 0.0 |
| 10%(K/Mo = 1)/Si:Ti 1:1 | 88.5 | 10.6 | 0.0 | 0.4 | 0.1 | 0.4 |
| 10%(K/Mo = 2)/Si:Ti 1:1 | 85.6 | 10.0 | 0.0 | 2.5 | 2.0 | 0.0 |

TABLE 4-continued

Reaction Comparison for 10%(K/Mo)/Si:Ti 1:1 Catalysts With Different K/Mo Ratios at Equal Propane Conversion

| | Selectivity | | | | | |
|---|---|---|---|---|---|---|
| | $C_3H_6$(%) | $CO_2$(%) | CO(%) | $C_2H_4$(%) | $CH_4$(%) | $C_2H_6$(%) |
| ~10% Propane Conversion | | | | | | |
| 10%(Mo)/Si:Ti 1:1 | 79.3 | 7.0 | 13.6 | 0.1 | 0.0 | 0.0 |
| 10%(K/Mo = 0.07)/Si:Ti 1:1 | 88.5 | 5.0 | 6.4 | 0.1 | 0.0 | 0.0 |
| 10%(K/Mo = 0.14)/Si:Ti 1:1 | 88.0 | 7.5 | 4.3 | 0.1 | 0.1 | 0.0 |
| 10%(K/Mo = 0.3)/Si:Ti 1:1 | 91.7 | 4.9 | 3.3 | 0.1 | 0.0 | 0.0 |
| 10%(K/Mo = 0.6)/Si:Ti 1:1 | 89.0 | 7.4 | 0.0 | 2.4 | 1.3 | 0.0 |
| 10%(K/Mo = 1)/Si:Ti 1:1 | 87.3 | 6.8 | 0.0 | 3.3 | 2.6 | 0.0 |
| 10%(K/Mo = 2)/Si:Ti 1:1 | | | Did not reach 10% | | | |

Conditions: 450° C., % $N_2/C_3/O_2$: 61/26/13, 25 cc/min.

product stream. Experiments were also performed using a more dilute propane concentration to obtain higher yields, ($N_2/C_3H_8/O_2$:92.5%/5%/12.5. Using this feed concentration, the performances of two of the catalysts with highest propylene selectivity (K/Mo ratios of 0.07 and 0.3) were compared to those of the potassium-free catalyst and of the bare Si:Ti support.

A set of pre-hydrolyzed catalysts with a constant K/Mo ratio of 2 were compared to the "stoichiometrically" hydrolyzed catalyst in regard to their ODH behavior. Selectivities obtained at an equal conversion of ~3% and a temperature of 500° C. are presented in Table 5. When the silica precursor is prehydrolyzed keeping the other synthesis parameters the same, we observe an appreciable increase in propylene selectivity compared to the catalysts prepared without any prehydrolysis step. However, changing the preparation parameters, such acidity or the speed of addition of the aqueous solutions for the prehydrolyzed catalyst does not appear to have much effect on propylene

TABLE 5

Effect of Hydrolysis Conditions for 10% (K/Mo = 2)/Si:Ti 1:1 Catalysts

| | Selectivity | | | | |
|---|---|---|---|---|---|
| | $C_3H_6$ (%) | $CO_2$ (%) | CO (%) | $C_2H_4$ (%) | $CH_4$ (%) |
| Hydrolyzed | 83.2 | 15.5 | 0.0 | 1.1 | 0.1 |
| Prehydrolyzed | 90.0 | 8.6 | 0.0 | 1.4 | 0.0 |
| Prehydrolyzed Fast Addition | 73.5 | 24.2 | 0.0 | 2.2 | 0.0 |
| Prehydrolyzed Acidic (pH = 3) | 66.9 | 28.2 | 0.0 | 4.9 | 0.0 |
| Prehydrolyzed Basic (pH = 11) | 77.3 | 13.3 | 7.1 | 2.0 | 0.3 |

Conditions: ~3% propane conversion, 500° C., % $N_2/C_3/O_2$ 92.5/5/2.5, 25 cc/min.

selectivity. Another point worth noting about these comparisons is the fact that catalysts prepared without pH control (with or without prehydrolysis) show the lowest $CO_2$ and ethylene selectivities.

Figure 7:
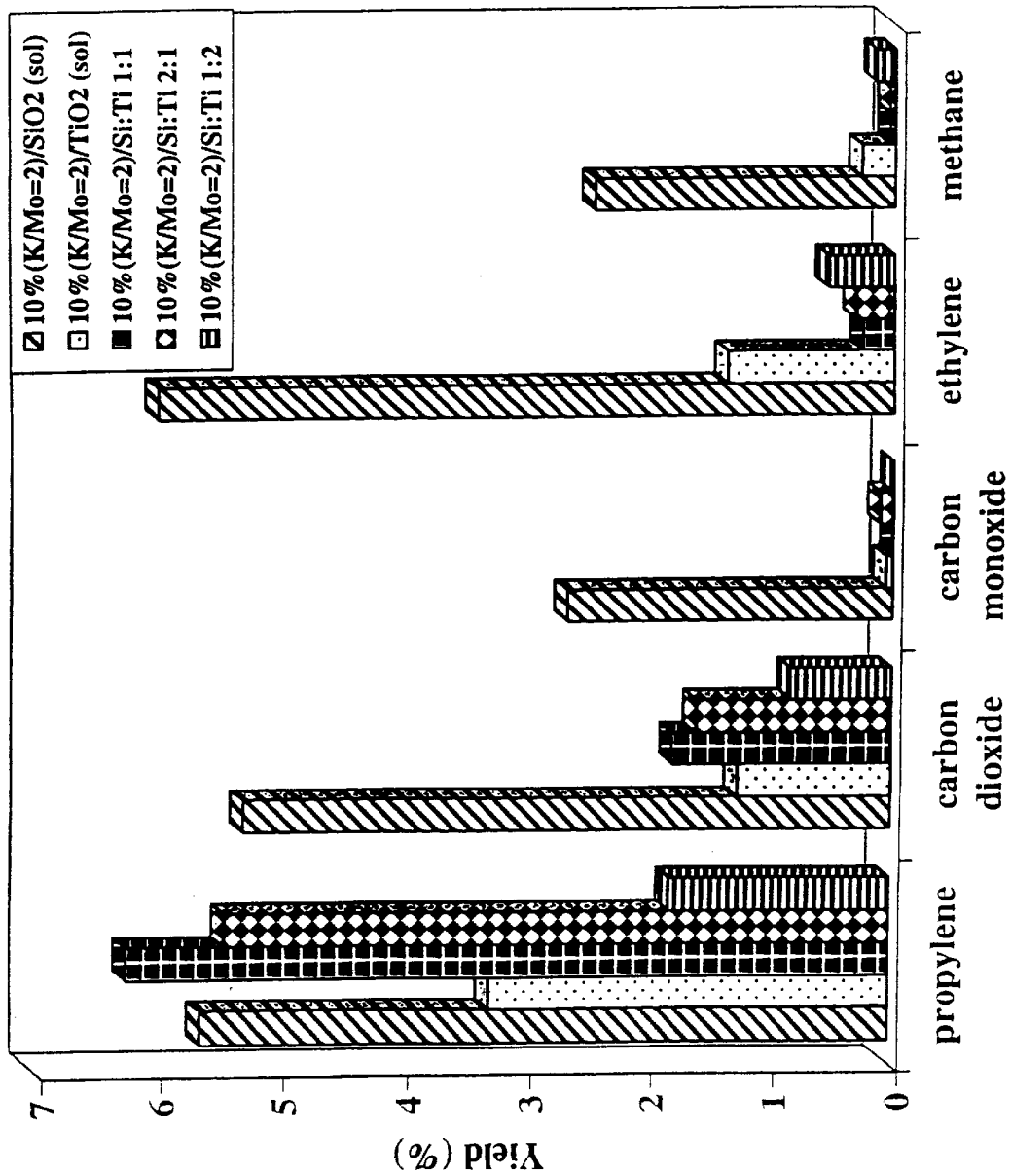
FIG. 7 shows the effect of Si:Ti molar ratio of 10% (K/Mo=2)/Si:Ti 1:1 catalysts on yield, constant Mo loading (0.1 g), 550° C., % $N_2/C_3/O_2$ 92.5/5/2.5, 25 cc/min, in accordance with one embodiment of the present invention.

To investigate the effect of the support composition, catalysts with different Si:Ti ratios were compared using 10% Mo loading and a K/Mo ratio of 2. The comparison was based on equal mass of Mo metal in the reactor. The temperature for these reactions was 550° C. The yields of different reaction products obtained are presented in FIG. 7. There was no $C_2H_6$ observed in these runs. The highest propylene yield was obtained over the catalysts that had a Si:Ti ratio of 1:1. This catalyst showed no CO or $CH_4$ formation and very little $CO_2$ and $C_2H_4$ formation. The propylene yield for the Si-rich catalysts also appear to give relatively high yields for propylene, but these are accompanied by high yields for CO, $CO_2$, $C_2H_4$ and $CH_4$.

Homogeneous volume minimization downstream from reactor or free-radical quenching is necessary in propane ODH reaction to isolate catalytic activity from gas phase activity. Radicals, once formed on the surface of the catalyst, can desorb during reaction and contribute to gas phase pyrolysis downstream from the catalyst bed. To examine the contribution of homogeneous reaction, experiments were performed with and without dead volume packing downstream from the reactor. Our results showed this effect to be important even at 400° C. Experiments performed using the K/Mo=0.07 catalyst and a feed stream ((%$N_2/C_3/O_2$:92.5%/5%/2.5%).) of 25 cm$^3$/min flow rate showed that the propane conversion increased from 13 to 16% when packing downstream from the catalyst bed was removed.

Figure 8:
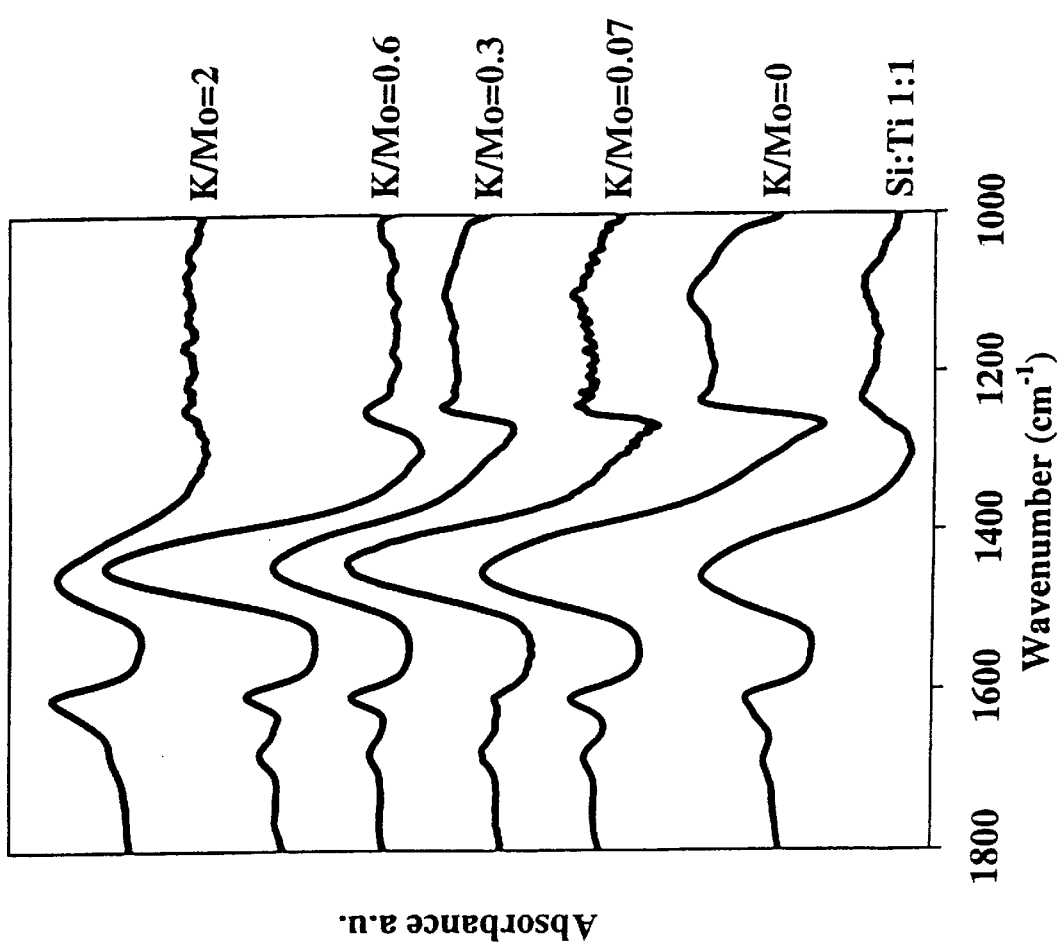
FIG. 8 shows adsorbed $NH_3$ IR bands over 10% (K/Mo)/Si:Ti 1:1 catalysts and bare support, in accordance with one embodiment of the present invention.

The IR spectra of ammonia species formed on 10%Mo/Si:Ti 1:1 catalysts with different K/Mo ratios, are shown in FIG. 8. The bands listed in Table 6 characterize the spectra. Bands commonly used to characterize Lewis and Brønsted acidity are those located at ~1607 cm$^{-1}$ (Lewis) and ~1448 cm$^{-1}$ (Brønsted). In Table 6, an attempt to quantify the Lewis and Brønsted characteristics of the catalysts is made using these peak areas and intensities. Compared to the Si:Ti support, the K/Mo=0 catalyst has considerably more Brønsted acid character and similar Lewis acid character. With the addition of potassium to the catalyst, the Lewis acid character decreases to a minimum at K/Mo=0.07 and sharply increases at K/Mo=2.

Figure 9:
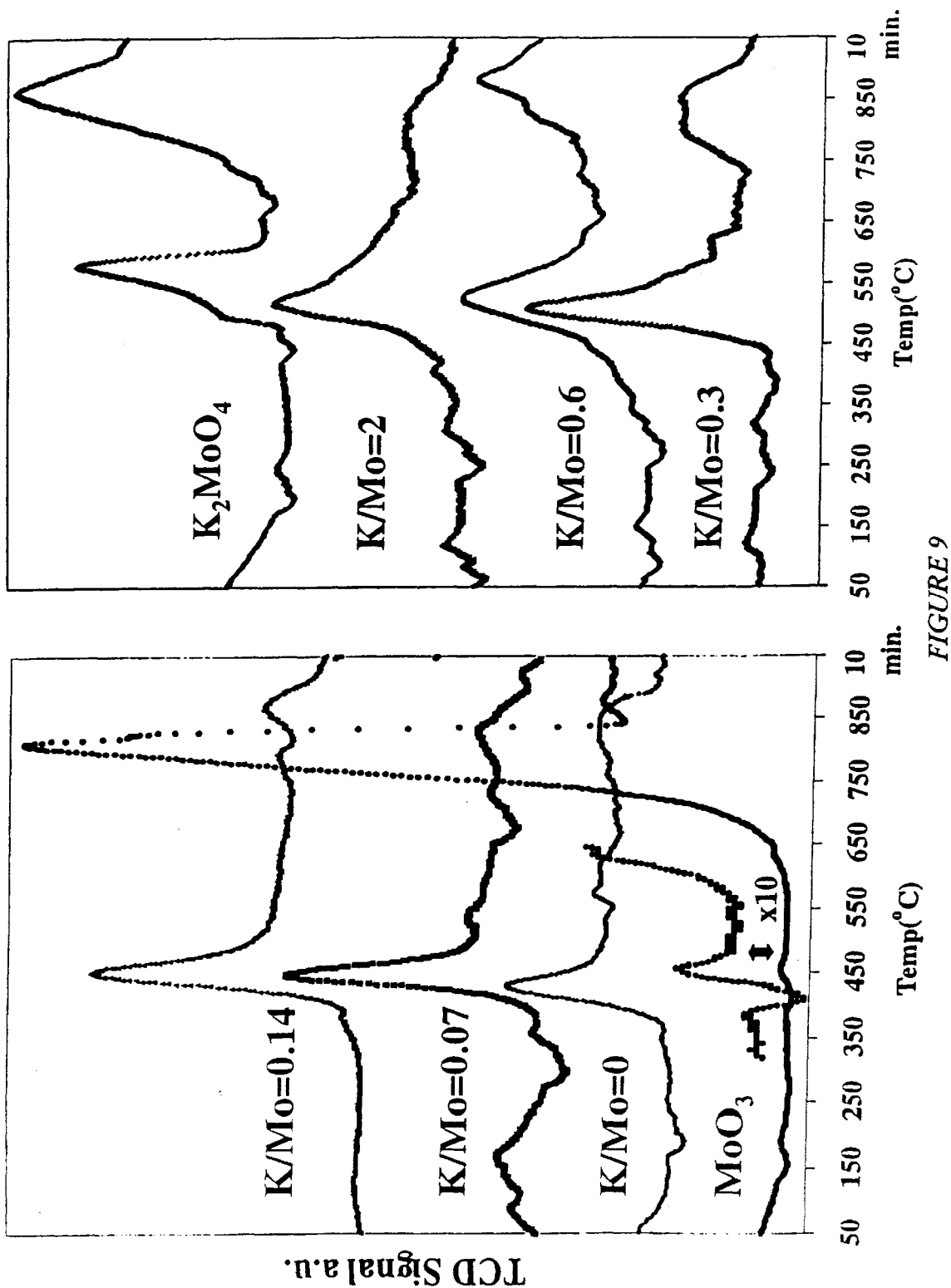
FIG. 9 shows the temperature programmed reduction profiles for 10% (K/Mo)/Si:Ti 1:1 catalysts, 10% $H_2/N_2$, in accordance with one embodiment of the present invention.

Temperature Programmed Reduction experiments were performed on catalysts with different K/Mo ratios. The results are compared to bulk $MoO_3$ and $K_2MoO_4$ samples prepared from the same precursors as the synthesized catalysts. The results are plotted in FIG. 9. The profiles for supported K/Mo catalysts are similar, consisting of one major temperature maximum in the 400–500° C. range. As the K/Mo ratio increases, the maxima begin to shift to higher temperatures and the peaks show considerable broadening. At K/Mo ratios of 0.6 and higher, we begin to see peaks becoming very noticeably asymmetrical, possibly representing two different reduction sites.

TABLE 6

NH₃ IR Adsorption Bands

| Band (cm⁻¹) Acidity | | Assignment |
|---|---|---|
| 1074–1082 | H-Bonded NH₃ | NH₂ Rocking |
| 1220–1248 | Lewis | N—N Streching |
| 1450–1434 | Brønsted | NH₂ Wagging |
| 1604–1607 | Lewis | NH₂ Scissoring |
| 1670–1680 | Brønsted | NH₂ Scissoring | baseline corrected peak areas

| K/Mo Ratio | Lewis ~1607 cm⁻¹ | Brønsted ~1448 cm⁻¹ | Area B/Area L | % Lewis* |
|---|---|---|---|---|
| Si:Ti 1:1 | 6.4 | 26.1 | 4.1 | 20 |
| 0 | 6.8 | 42.4 | 6.3 | 14 |
| 0.07 | 1.3 | 32.7 | 25.0 | 4 |
| 0.3 | 5.1 | 34.0 | 6.6 | 13 |
| 0.6 | 1.1 | 9.4 | 8.8 | 10 |
| 2 | 5.7 | 15.3 | 2.7 | 27 |

*calculated with peak areas

When these profiles are compared to that of bulk $K_2MoO_4$, we see that the temperature for this secondary feature, which appears as a large shoulder, coincides with the major reduction peak observed over the bulk $K_2MoO_4$. Table 7 summarizes the temperature maxima and the FWHM (Full Width at Half Maximum) of these major reduction peaks. Analysis of the desorbed species after propane adsorption showed propane, propylene, water, $CO_2$, CO, $O_2$, and trace amounts of methane, ethane, and acrolein desorbing from the surface.

TABLE 7

Temperature Programmed Reduction of 10% (K/Mo)/Si:Ti 1:1 Catalysts With Different K/Mo Ratios

| Catalyst | 1st peak Maxima (° C.) | FWHM (° C.) |
|---|---|---|
| MoO₃ | 459 | 34 |
| K/Mo = 0 | 436 | 58 |
| K/Mo = 0.07 | 450 | 46 |
| K/Mo = 0.14 | 456 | 53 |
| K/Mo = 0.3 | 512, 560 sh | 75 |
| K/Mo = 0.6 | 531, 566 sh | 104 |
| K/Mo = 2 | 520, 570 sh | 118 |
| K₂MoO₄ | 531 | 54 | sh = shoulder

Figure 10:
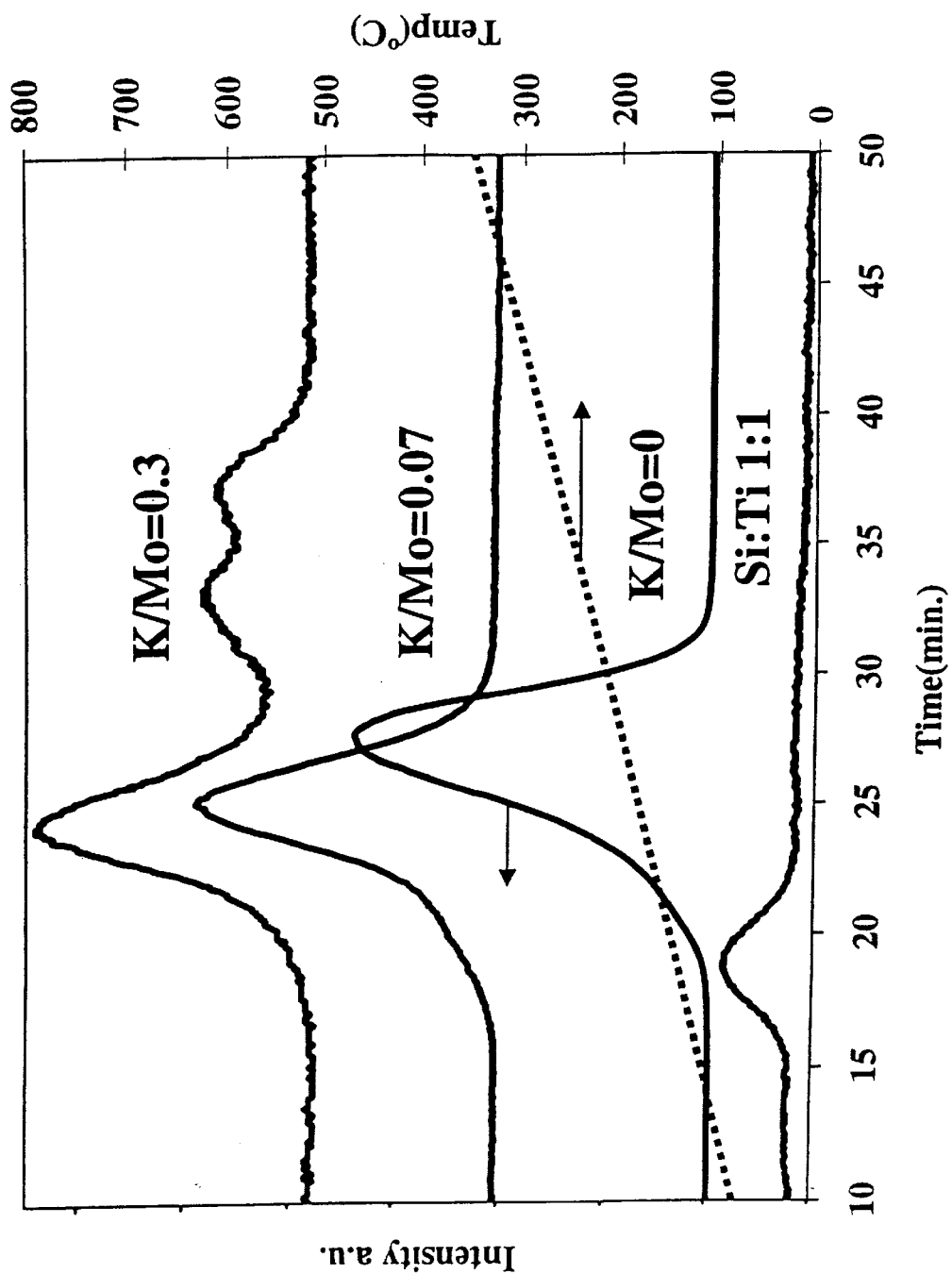
FIG. 10 shows propane temperature programmed desorption: propene desorption profiles over 10% (K/Mo)/Si:Ti 1:1 catalysts, in accordance with one embodiment of the present invention.
Figure 11:
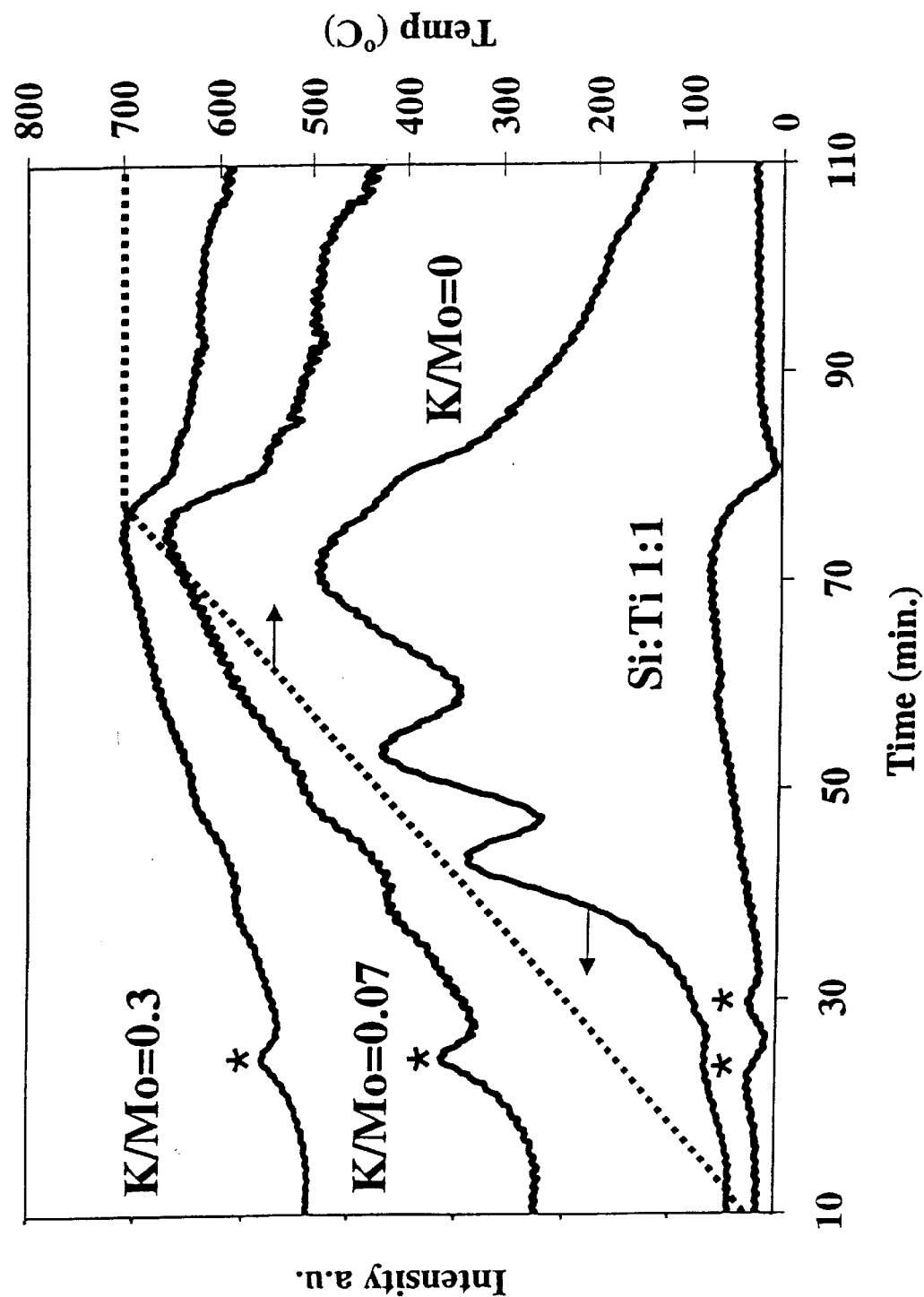
FIG. 11 shows propane temperature programmed desorption: carbon monoxide desorption profiles over 10% (K/Mo)/Si:Ti 1:1 catalysts (*=ethylene desorption), in accordance with one embodiment of the present invention.

Propylene desorption profiles for the Si:Ti 1:1 support, 10%Mo/Si:Ti 1:1, and potassium containing catalysts of K/Mo=0.07 and 0.3 are plotted in FIG. 10. Focusing on the "molybdenum only" catalyst, there is one desorption feature with peak maximum temperature around 200° C. An important aspect of these profiles is that the first desorption feature shifts to lower temperatures with increasing potassium loading. The water desorption profiles follow the propylene desorption closely, indicating that propylene formation takes place oxidatively, using the lattice oxygen. The shift of the propylene desorption peaks to lower temperatures also points to an ease of desorption from the surface for the potassium containing catalysts. With the addition of potassium, two additional sites for propylene desorption are formed on the K/Mo=0.3 catalyst at higher temperatures (~260 and ~300° C.). The desorption profiles for carbon monoxide for the same catalysts are plotted in FIG. 11. Although ethylene has the same molecular weight as carbon monoxide, by following fragments created by both, we determined that the first desorption peaks (<200° C.) are associated with ethylene desorption and the remainder of the profile belongs to carbon monoxide alone. There are three significant desorption features present on the "molybdenum only" catalyst at 360, 465, and 650° C. With the addition of potassium, these desorption features appear to be suppressed and less pronounced in a broad profile.

Figure 12:
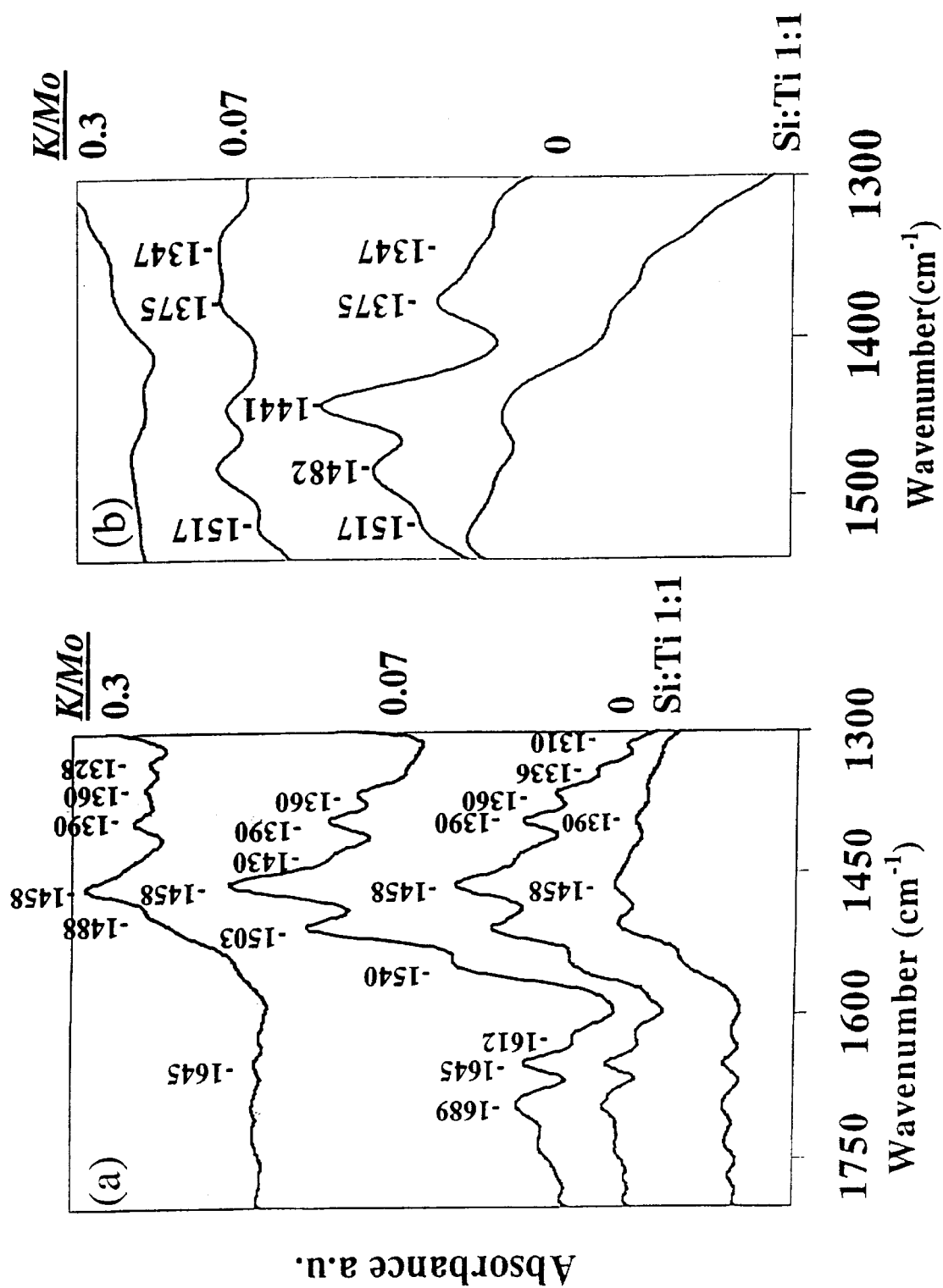
FIG. 12 shows (a) In situ DRIFT spectra of 10% (K/Mo)/Si:Ti 1:1 catalysts, 450° C. surface temperature, % $N_2/C_3/O_2$:61/26/13 (b) DRIFT spectra of 10% (K/Mo)/Si:Ti 1:1 catalysts after quenching under $N_2$, in accordance with one embodiment of the present invention.

To ascertain the differences in reaction intermediates present on the catalyst during reaction conditions, IR spectra of adsorbed species were obtained at 450° C. surface temperature. After gas phase spectra subtraction, the results are plotted in FIG. 12(a) in the range 1800–1300 cm⁻¹. Similar bands are observed on the K/Mo catalysts studied. Band observed around 1689 cm⁻¹ is associated with adsorbed acetone. Bands located around 1540, 1503, 1430, 1360, and 1328–1336 cm⁻¹ are associated with acetate, formate, π-allyl, and acrolein type species. Olefinic $CH_x$ stretches are located at 1458 and 1390 cm⁻¹. Two interesting features to note in FIG. 12(a) are that the highest yield ODH catalyst of this study, K/Mo=0.07, shows the most intense olefinic $CH_x$ stretching bands. Furthermore, one of the most selective ODH catalysts, K/Mo=0.3, shows a lack of intensity from the acetate and formate species present on the other catalysts. This agrees well with the reaction results as these intermediates may lead to the formation of $CO_x$ products. In FIG. 12(b), the IR spectra are shown after the reaction has been quenched to room temperature under nitrogen. It is apparent that olefinic species are still present on the "molybdenum only" catalyst, indicated by the bands at 1441 and 1375 cm⁻¹, which have shifted to lower wavenumbers with the decrease in temperature of the sample surface. Over the potassium-containing catalysts, on the other hand, these bands have essentially disappeared. Again, this suggests a weaker adsorption of propylene on the surface, leading to easier desorption.

The preferred embodiments herein disclosed are not intended to be exhaustive or to unnecessarily limit the scope of the invention. The preferred embodiments were chosen and described in order to explain the principles of the present invention so that others skilled in the art may practice the invention. Having shown and described preferred embodiments of the present invention, it will be within the ability of one of ordinary skill in the art to make alterations or modifications to the present invention, such as through the substitution of equivalent compounds or through the use of equivalent process steps, so as to be able to practice the present invention without departing from its spirit as reflected in the appended claims, the text and teaching of which are hereby incorporated by reference herein. It is the intention, therefore, to limit the invention only as indicated by the scope of the claims and equivalents thereof.

What is claimed is:

1. A sol-gel supported catalyst for the dehydrogenation of lower alkanes, said catalyst comprising at least one active metal and at least one promoter metal attached to a sol-gel mixed oxide support, said sol-gel mixed oxide support arising from the polymerization of at least one precursor thereof, said at least one active metal and said at least one promoter metal having been attached to said sol-gel mixed oxide support by said at least one active metal and at least one promoter metal having been co-precipitated with said precursor of said sol-gel mixed oxide support.

2. A sol-gel supported catalyst according to claim 1 wherein said at least one active metal is selected from the group consisting of vanadium and molybdenum, and mixtures thereof.

3. A sol-gel supported catalyst according to claim 1 wherein said at least one active metal is added to the catalyst in amounts of from about 1% to about 20% by weight.

4. A sol-gel supported catalyst according to claim 1 wherein said sol-gel mixed oxide support comprises titanium oxide and silicon oxide, and wherein the molar ratio of said titanium oxide to said silicon oxide is about 1:1.

5. A sol-gel supported catalyst according to claim 1 wherein said precursor of said mixed oxide support is selected from the group consisting of silicon alkoxide and titanium alkoxide.

6. A sol-gel supported catalyst according to claim 5 wherein said precursor of said mixed oxide support comprises silicon alkoxide and titanium alkoxide, and wherein said silicon alkoxide is of the formula $Si(OR_1)_4$ and said titanium alkoxide is of the formula $Ti(OR_1)_4$, wherein $R_1$ is selected from methyl, ethyl, n-propyl, isopropyl, and butyl groups.

7. A sol-gel supported catalyst according to claim 1 wherein said at least one promoter metal is an alkali metal selected from the group consisting of Li, Na, K, Rb, and Cs.

8. A sol-gel supported catalyst according to claim 1 wherein said active metal comprises molybdenum and said promoter metal comprises an alkali metal, and the molar ratio of said alkali metal to said molybdenum is in the range of from about 0:1 to about 2:1.

9. A sol-gel supported catalyst according to claim 8 wherein said molar ratio of said alkali metal to said molybdenum is about 0.1:1.

10. A method of producing a sol-gel supported catalyst, said method comprising:
    (a) obtaining a sol-gel precursor solution comprising at least one silicon alkoxide and at least one titanium alkoxide in a solvent;
    (b) adding to said sol-gel precursor solution at least one active metal-containing precursor in aqueous solution and at least one promoter metal-containing precursor in aqueous solution; and
    (c) allowing said at least one silicon alkoxide and at least one titanium alkoxide to become polymerized to form a sol-gel while allowing said at least one active metal-containing precursor and said at least one promoter metal-containing precursor to precipitate.

11. A method according to claim 10 wherein the molar ratio of titanium alkoxide to silicon alkoxide in said sol gel is about 1:1.

12. A method according to claim 10 wherein said silicon alkoxide is of the formula $Si(OR_1)_4$, wherein $R_1$ is selected from methyl, ethyl, n-propyl, isopropyl and butyl groups.

13. A method according to claim 10 wherein said titanium alkoxide is of the formula $Ti(OR_1)_4$, wherein $R_1$ is selected from methyl, ethyl, n-propyl, isopropyl, and butyl groups.

14. A method according to claim 10 wherein said at least one promoter metal is an alkali metal selected from the group consisting of Li, Na, K, Rb, and Cs.

15. A method according to claim 10 wherein said active metal comprises molybdenum and said promoter metal comprises an alkali metal, and the molar ratio of said alkali metal to said molybdenum is in the range of from about 0:1 to about 2:1.

16. A method according to claim 15 wherein said molar ratio of said alkali metal to said molybdenum is about 0.1:1.

17. A method according to claim 10 wherein said at least one active metal-containing precursor is selected from the group consisting of ammonium heptamolybdate, molybdenum isopropoxide, vanadium pentaoxide, and vanadium acetate.

18. A method according to claim 10 wherein said at least one promoter metal-containing precursor is selected from the group consisting of alkali carbonates, alkali nitrates, alkali hydroxides, and alkali chlorides.

19. The method according to claim 10 wherein said solvent is selected from a pure or mixed alcohol from the group consisting of methanol, ethanol, propanol and isopropanol.

20. A method of dehydrogenating lower alkanes to produce lower alkenes using a catalyst, said method comprising the steps:
    (a) obtaining a sol-gel supported catalyst, said catalyst comprising at least one active metal and at least one promoter metal attached to a sol-gel mixed oxide support, said sol-gel mixed oxide support arising from the polymerization of at least one precursor thereof, said at least one active metal and said at least one promoter metal having been attached to said sol-gel mixed oxide support by said at least one active metal and at least one promoter metal having been co-precipitated with said precursor of said sol-gel mixed oxide support; and
    (b) bringing into contact with said catalyst at least one lower alkane for sufficient time and at sufficient temperature so as to allow said at least one lower alkane to be dehydrogenated.

21. A method according to claim 20 wherein said sol-gel mixed oxide support comprises titanium oxide and silicon oxide, and wherein the molar ratio of said titanium oxide to said silicon oxide is about 1:1.

22. A method according to claim 20 wherein said active metal comprises molybdenum and said promoter metal comprises an alkali metal, and the molar ratio of said alkali metal to said molybdenum is in the range of from about 0:1 to about 2:1.

23. A method according to claim 20 wherein said molar ratio of said alkali metal to said molybdenum is about 0.1:1.

* * * * *

UNITED STATES PATENT AND TRADEMARK OFFICE
CERTIFICATE OF CORRECTION

PATENT NO. : 6,521,808 B1
APPLICATION NO. : 09/506677
DATED : February 18, 2003
INVENTOR(S) : Ozkan et al.

Page 1 of 1

It is certified that error appears in the above-identified patent and that said Letters Patent is hereby corrected as shown below:

In the Specification

Line 5, before the heading "TECHNICAL FIELD OF THE INVENTION" please add:
"STATEMENT REGARDING FEDERALLY SPONSORED RESEARCH OR DEVELOPMENT
This invention was made with government support under grant number 9412544 awarded by the National Science Foundation. The government has certain rights in the invention."

Signed and Sealed this
Sixth Day of October, 2020

Andrei Iancu
*Director of the United States Patent and Trademark Office*